US012213826B2

(12) United States Patent
Li et al.

(10) Patent No.: US 12,213,826 B2
(45) Date of Patent: Feb. 4, 2025

(54) SYSTEMS AND METHODS FOR DETERMINING TRUE COINCIDENCE EVENTS

(71) Applicant: SHANGHAI UNITED IMAGING HEALTHCARE CO., LTD., Shanghai (CN)

(72) Inventors: Jun Li, Shanghai (CN); Wei Zheng, Shanghai (CN); Longzi Yang, Shanghai (CN); Shitao Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 447 days.

(21) Appl. No.: 17/450,837

(22) Filed: Oct. 14, 2021

(65) Prior Publication Data
US 2022/0031272 A1 Feb. 3, 2022

Related U.S. Application Data

(63) Continuation of application No. PCT/CN2020/084861, filed on Apr. 15, 2020.

(30) Foreign Application Priority Data

Apr. 15, 2019 (CN) .......................... 201910299086.5
Jun. 13, 2019 (CN) .......................... 201910511146.5
Sep. 4, 2019 (CN) .......................... 201910833121.7

(51) Int. Cl.
*A61B 6/00* (2024.01)
*A61B 6/03* (2006.01)
(Continued)

(52) U.S. Cl.
CPC ............ *A61B 6/5205* (2013.01); *A61B 6/037* (2013.01); *A61B 6/4266* (2013.01); *G06T 11/005* (2013.01); *G04F 10/005* (2013.01)

(58) Field of Classification Search
None
See application file for complete search history.

(56) References Cited

U.S. PATENT DOCUMENTS 6,674,083 B2   1/2004   Tanaka et al.
7,863,573 B2   1/2011   Aoki
(Continued)

FOREIGN PATENT DOCUMENTS

CN   101268949 A   9/2008
CN   202173405 U   3/2012
(Continued)

OTHER PUBLICATIONS

The Extended European Search Report in European Application No. 20791156.1 mailed on Apr. 29, 2022, 7 pages.
(Continued)

*Primary Examiner* — Edwin C Gunberg
(74) *Attorney, Agent, or Firm* — METIS IP LLC

(57) ABSTRACT

The present disclosure relates to systems and methods for determining true coincidence events. The systems and methods may determine original coincidence events based on time of occurrence of a plurality of single events. The systems and methods may also determine random coincidence events by processing the plurality of single events based on cycle offsets of detector units that detect the plurality of single events. A difference of any two cycle offsets may be greater than a predetermined coincidence window width. The systems and methods may then determine the true coincidence events based on the original coincidence events and the random coincidence events.

19 Claims, 21 Drawing Sheets

(51) Int. Cl.
*A61B 6/42* (2024.01)
*G04F 10/00* (2006.01)
*G06T 11/00* (2006.01)

(56) References Cited

U.S. PATENT DOCUMENTS

| | | | |
|---|---|---|---|
| 9,176,237 | B2 | 11/2015 | Yoshida et al. |
| 11,280,921 | B2* | 3/2022 | Niu ............... G01T 1/2985 |
| 2003/0108229 | A1 | 6/2003 | Tanaka et al. |
| 2006/0151705 | A1 | 7/2006 | Manjeshwar et al. |
| 2011/0274241 | A1* | 11/2011 | Ohtani ............. G01T 1/2985 |
| | | | 378/22 |
| 2017/0046857 | A1 | 2/2017 | Ye et al. |
| 2018/0123773 | A1 | 5/2018 | Cui et al. |
| 2018/0144513 | A1 | 5/2018 | Liu et al. |
| 2019/0076110 | A1 | 3/2019 | Moriyasu |
| 2020/0363541 | A1 | 11/2020 | Li et al. |
| 2020/0405247 | A1 | 12/2020 | Gu et al. |
| 2021/0356610 | A1 | 11/2021 | Niu et al. |

FOREIGN PATENT DOCUMENTS

| | | |
|---|---|---|
| CN | 102631212 A | 8/2012 |
| CN | 104111468 A | 10/2014 |
| CN | 104224219 A | 12/2014 |
| CN | 105450215 A | 3/2016 |
| CN | 106691486 A | 5/2017 |
| CN | 107464270 A | 12/2017 |
| CN | 108013895 A | 5/2018 |
| CN | 109350099 A | 2/2019 |
| CN | 109998582 A | 7/2019 |
| CN | 110269637 A | 9/2019 |
| CN | 110507344 A | 11/2019 |
| JP | 2011185716 A | 9/2011 |

OTHER PUBLICATIONS

Wang, Chao et al., A Low-Cost Coincidence System with Capability of Multiples Coincidence for High Count-Rate TOF or Non-TOF PET Cameras Using Hybrid Method Combining AND-logic and Time-mark Technology, IEEE Nuclear Science Symposium Conference Record, 3633-3638, 2009.
International Search Report in PCT/CN2020/084861 mailed on Jul. 16, 2020, 5 pages.
Written Opinion in PCT/CN2020/084861 mailed on Jul. 16, 2020, 6 pages.
First Office Action in Chinese Application No. 201910299086.5 mailed on Mar. 3, 2021, 20 pages.
First Office Action in Chinese Application No. 201910511146.5 mailed on Dec. 16, 2020, 16 pages.
The Second Office Action in Chinese Application No. 201910511146.5 mailed on May 31, 2021, 12 pages.
The Third Office Action in Chinese Application No. 201910511146.5 mailed on Sep. 13, 2021, 17 pages.
First Office Action in Chinese Application No. 201910833121.7 mailed on Mar. 3, 2021, 22 pages.
Wang, Chao et al., A Real Time Coincidence System for High Count-Rate TOF or Non-TOF PET Cameras Using Hybrid Method Combining AND-Logic and Time-Mark Technology, IEEE Transactions on Nuclear Science, 57(2): 708-714, 2010.
Zhang, Yuxuan et al., The Systematic Errors in the Random Coincidence Estimation Using a Delayed Window, 2009 IEEE Nuclear Science Symposium Conference Record, 3897-3899, 2009.
Wang, Xuyi, Explanation and Analysis of Measurement Results, Computer System Performance Evaluation, 1992, 5 pages.

* cited by examiner

SYSTEMS AND METHODS FOR DETERMINING TRUE COINCIDENCE EVENTS

CROSS-REFERENCE TO THE RELATED APPLICATIONS

This application is a Continuation of PCT Application No. PCT/CN2020/084861, filed on Apr. 15, 2020, which claims priority of Chinese Application No. 201910299086.5, filed on Apr. 15, 2019, and Chinese Application No. 201910511146.5, filed on Jun. 13, 2019, and Chinese Application No. 201910833121.7, filed on Sep. 4, 2019, the contents of each of which are hereby incorporated by reference.

TECHNICAL FIELD

The present disclosure generally relates to positron emission tomography (PET) imaging, and more specifically relates to systems and methods for determining true coincidence events during the PET imaging.

BACKGROUND

Positron emission tomography (PET) is an imaging technique commonly used in clinical medicine and biomedical research. Each PET session produces two-dimensional or three-dimensional images of functional processes in a target organ or tissue of a body. Specifically, in PET studies, a biologically active molecule carrying a radioactive tracer is first introduced into a subject's body. The PET system then detects pairs of gamma rays, whose emissions are caused by the radioactive tracer, and reconstructs images showing the tracer concentration within the body by analyzing the detected signals. Because the biologically active molecules used in PET studies are natural substrates of metabolism at the target organ or tissue, PET can evaluate the physiology (functionality) of the target organ or tissue, as well as its biochemical properties.

PET imaging is based on coincidence events corresponding to detected gamma photons arising from positron-electron annihilation. A true coincidence event includes a pair of corresponding single events, in which two gamma photons arise from a same positron-electron annihilation. However, the coincidence events recorded by a PET scanner generally include true coincidence events, scattered events, and random events. The existence of the scattered events and random events may degrade the sensitivity and resolution of the PET. Thus, it is desirable to provided systems and methods for determining the true coincidence events, thus improving the accuracy and efficiency of the PET technology.

SUMMARY

According to one aspect of the present disclosure, a device for determining coincidence events in a PET system is provided. The device may include one or more detector rings; and one or more coincidence modules, each corresponding to each of the one or more detector rings, respectively. The one or more coincidence modules may be configured to determine coincidence events based on single events detected by the one or more detector rings. The coincidence events determined by a coincidence module may include first coincidence events and second coincidence events. A first coincidence event may include two first single events that are corresponding to each other. A second coincidence event may include a first single event and a second single event. The first single event may be a single event from a detector ring corresponding to the coincidence module and the second single event may be a single event from a detector ring not corresponding to the coincidence module.

In some embodiments, the coincidence module may include a first coincidence unit and a second coincidence unit. The first coincidence unit may be configured to obtain multiple first single events and determine multiple first coincidence events based on the multiple first single events. The second coincidence unit may be configured to obtain multiple first single events and multiple second single events and determine multiple second coincidence events based on the multiple first single events and the multiple second signal events.

In some embodiments, the device may further include at least one reconstruction module, wherein the at least one reconstruction module is connected to the one or more coincidence modules and is configured to receive the coincidence events and reconstruct an image based on the coincidence events.

In some embodiments, the device may further include a control and transmission module, wherein the control and transmission module is disposed between the one or more coincidence modules and the at least one reconstruction module and is configured to receive the coincidence events and transmit the coincidence events to the at least one reconstruction module.

In some embodiments, the device may further include a control module, wherein the control module is connected to the control and transmission module and is configured to transmit an instruction to the control and transmission module.

In some embodiments, the device may further include an interconnection module connected to the one or more coincidence modules, wherein the interconnection module is configured to store the single events detected by the one or more detector rings, and a coincidence module is configured to obtain second single events from the interconnection module.

In some embodiments, the interconnection module may include an interconnection matrix.

According to another aspect of the present disclosure, a method for determining coincidence events is provided. The method may be implemented on a computing device including at least one processor, at least one storage device, and a communication platform connected to a network. The method may include obtaining single events detected by one or more detector rings, wherein the single events includes first single events and second single events, the first single events being a single event from a detector ring corresponding to a coincidence module and the second single event being a single event from a detector ring not corresponding to the coincidence module. The method may further include determining multiple first coincidence events based on the first single events and determining multiple second coincidence events based on the first single events and the second single events.

According to another aspect of the present disclosure, a PET system is provided. The PET system may include a processor, a gantry, a table, one or more detector rings, and one or more coincidence modules, each corresponding to each of the one or more detector rings, respectively. The one or more coincidence modules may be configured to determine coincidence events based on single events detected by the one or more detector rings. The one or more detector rings may be arranged along a detection tunnel of the gantry, each detector ring including a plurality of detector units arranged along a circumference of the detector ring.

According to another aspect of the present disclosure, a method for determining true coincidence events is provided. The method may be implemented on a computing device including at least one processor, at least one storage device, and a communication platform connected to a network. The method may include determining original coincidence events based on time of occurrence of a plurality of single events, determining random coincidence events by processing the plurality of single events based on cycle offsets of detector units that detect the plurality of single events, wherein a difference of any two cycle offsets is greater than a predetermined coincidence window width, and determining the true coincidence events based on the original coincidence events and the random coincidence events.

In some embodiments, the determining original coincidence events may include obtaining a cycle difference between a first clock cycle at which a first single event occurs and a second clock cycle at which a second single event occurs, obtaining a first time-to-digital converter (TDC) value of the first single event and a second TDC value of the second single event, determining a time difference between a time of occurrence of the first single event and a time of occurrence of the second single event based on the cycle difference, the first TDC value, and the second TDC value, and in response to a determination that the time difference is less than the predetermined coincidence window width, determining the first single event and the second single event as an original coincidence event.

In some embodiments, the determining a time difference between the time of occurrence of the first single event and the time of occurrence of the second single event may include determining a sequence that the first single event and the second single event occurs based on the cycle difference, determining a time difference determination formula based on the sequence, and determining the time difference between the time of occurrence of the first single event and the time of occurrence of the second single event according to the time difference determination formula.

In some embodiments, the method of claim 11 or claim 12, may further include: outputting the original coincidence event, which includes a time, an energy level, a location of the first single event and/or the second single event.

In some embodiments, the determining random coincidence events by processing the plurality of single events based on cycle offsets of detector units that detect the plurality of single events may include for each single event of the plurality of single events, obtaining a cycle offset of a detector unit that detect the single event, adjusting the time of occurrence of the single event by increasing the cycle offset to the time of occurrence of the single event, and determining the random coincidence events based on the adjustment of the time of occurrence of each single event.

In some embodiments, the cycle offset of the detector unit may include a coded value of the detector unit and a parameter value of the detector unit, wherein the coded values of different detector units are different.

In some embodiments, the parameter value of the detector unit is an integer multiple of a clock cycle and is greater than the predetermined coincidence window width.

In some embodiments, the plurality of single events are detected by one or more detector rings, and each of the one or more detector rings includes a plurality of detector units, wherein the coded value of a detector unit is expressed as $m*X+Y$, wherein m refers to the number of detector units of a detector ring, X refers to the serial number of detector ring, Y refers to the serial number of detector unit.

According to another aspect of the present disclosure, a system for determining true coincidence events is provided. The system may include at least one storage device including a set of instructions, and at least one processor in communication with the at least one storage device. When executing the set of instructions, the at least one processor may be configured to cause the system to determine original coincidence events based on time of occurrence of a plurality of single events, determine random coincidence events by processing the plurality of single events based on cycle offsets of detector units that detect the plurality of single events, wherein a difference of any two cycle offsets is greater than a predetermined coincidence window width, and determine the true coincidence events based on the original coincidence events and the random coincidence events.

According to another aspect of the present disclosure, a system for determining true coincidence events is provided. The system may include an original coincidence event determination module, a random coincidence event determination module and a true coincidence event determination module. The original coincidence event determination module may be configured to determine original coincidence events based on time of occurrence of a plurality of single events. The random coincidence event determination module may be configured to determine random coincidence events by processing the plurality of single events based on cycle offsets of detector units that detect the plurality of single events, wherein a difference of any two cycle offsets is greater than a predetermined coincidence window width. The true coincidence event determination module may be configured to determine the true coincidence events based on the original coincidence events and the random coincidence events.

According to another aspect of the present disclosure, a non-transitory computer-readable storage medium is provided. The storage medium may include at least one set of instructions. When executed by at least one processor of a computing device, the at least one set of instructions direct the at least one processor to perform acts of: determining original coincidence events based on time of occurrence of a plurality of single events, determining random coincidence events by processing the plurality of single events based on cycle offsets of detector units that detect the plurality of single events, wherein a difference of any two cycle offsets is greater than a predetermined coincidence window width, and determining the true coincidence events based on the original coincidence events and the random coincidence events.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by other expression if they achieve the same purpose.

Figure 2:
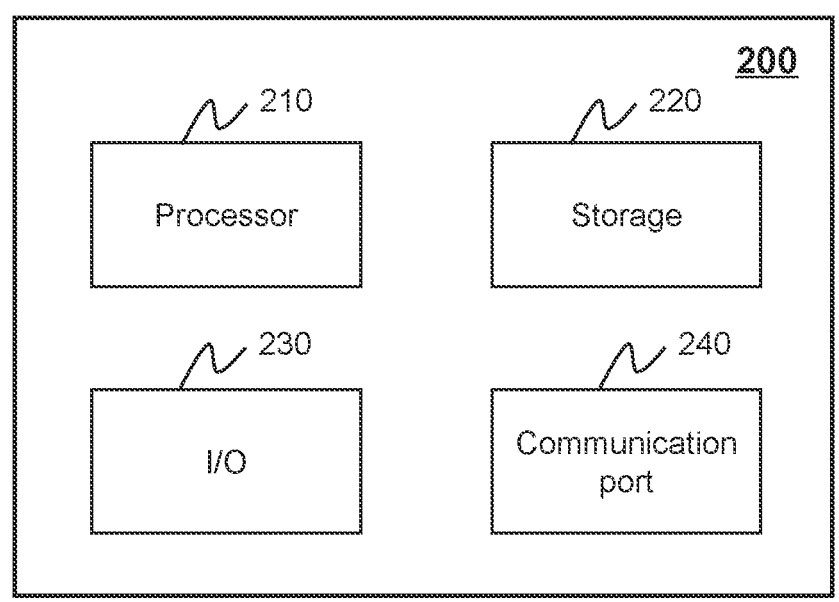
FIG. 2 is a schematic diagram illustrating exemplary hardware and/or software components of a computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to a device for determining coincidence events in a PET system. In some embodiments, the device may include one or more detector rings and one or more coincidence modules. Each coincidence module may correspond to a detector ring. The one or more coincidence modules may be configured to determine coincidence events based on single events detected by the one or more detector rings. The coincidence events determined by a coincidence module may include first coincidence events (also referred to as local coincidence events) and second coincidence events (also referred to as cross coincidence events). The first coincidence event may include two first single events that are corresponding to each other, and the second coincidence event may include a first single event and a second single event. The first single event may be a single event from a detector ring corresponding to the coincidence module and the second single event may be a single event from a detector ring not corresponding to the coincidence module.

Another aspect of the present disclosure relates to systems and methods for determining true coincidence events. The systems and methods may determine original coincidence events based on time of occurrence of a plurality of single events. The systems and methods may also determine random coincidence events by processing the plurality of single events based on cycle offsets of detector units that detect the plurality of single events. A difference of any two cycle offsets may be greater than a predetermined coincidence window width. The systems and methods may then determine the true coincidence events based on the original coincidence events and the random coincidence events.

Figure 1:
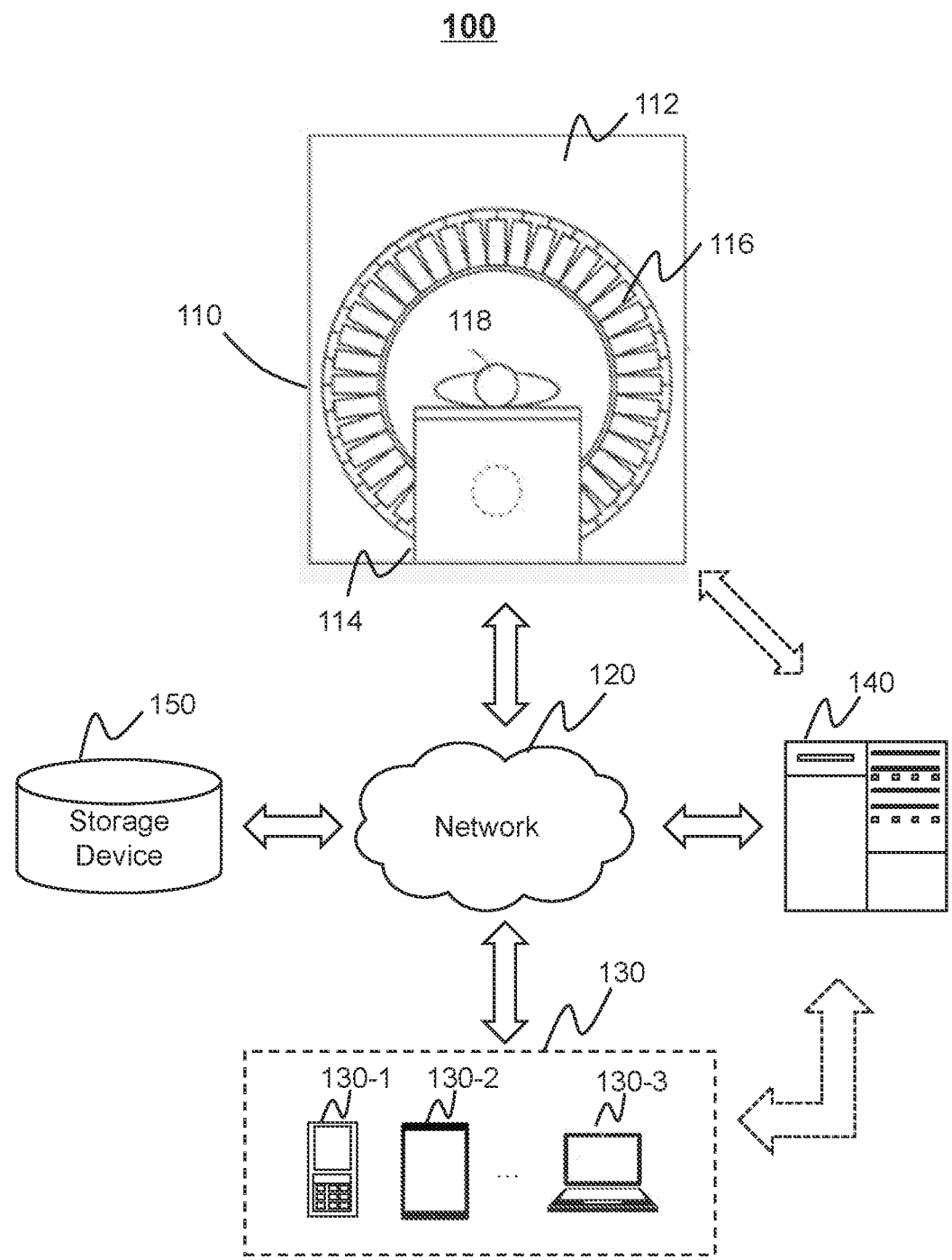
FIG. 1 is a schematic diagram illustrating an exemplary positron emission tomography (PET) system according to some embodiments of the present disclosure.

FIG. 1 is a schematic diagram illustrating an exemplary positron emission tomography (PET) system according to some embodiments of the present disclosure. PET imaging is based on coincidence events corresponding to detected photons arising from positron-electron annihilation. A true coincidence event includes a pair of corresponding single events, in which two gamma photons arise from a same positron-electron annihilation. As illustrated in FIG. 1, the PET system 100 may include a PET scanner 110, a network 120, a terminal 130, a processing device 140, and a storage device 150. The components in the PET system 100 may be connected in various ways. Merely by way of example, the PET scanner 110 may be connected to the processing device 140 through the network 120. As another example, the PET scanner 110 may be connected to the processing device 140 directly as indicated by the bi-directional arrow in dotted lines linking the PET scanner 110 and the processing device 140. As a further example, the storage device 150 may be connected to the processing device 140 directly or through the network 120. As still a further example, the terminal 130 (e.g., terminals 130-1, 130-2, 130-3, etc.) may be connected to the processing device 140 directly (as indicated by the bi-directional arrow in dotted lines linking the terminal 130 and the processing device 140) or through the network 120.

The PET scanner 110 may include a gantry 112, a table 114, a detector module 116. The gantry 112 may support the detector module 116. An object 118 may be placed on the table 114 and moved into a detection tunnel (not shown in FIG. 1) of the PET scanner 110. The object 118 may be a biological object (e.g., a patient, an animal) or a non-biological object. For example, the object 118 may include an organ (e.g., the heart, the stomach, the lungs, the liver, the kidney) of a patient, a body part (e.g., the head, the chest, the abdomen, the arm, the leg) of the patient, a tissue (e.g., the soft tissue) of the patient, a tumor in the patient, or the like, or any combination thereof. In the present disclosure, "object" and "subject" are used interchangeably. In some embodiments, the object 118 may be injected with a tracer before the PET scanning. The tracer may refer to a radioactive substance that may decay and emit positrons. In some embodiments, the tracer may be a radiopharmaceutical, which is a drug having radioactivity and is administered to the object 118 for the purposes of diagnosis and treatment.

Figure 4A:
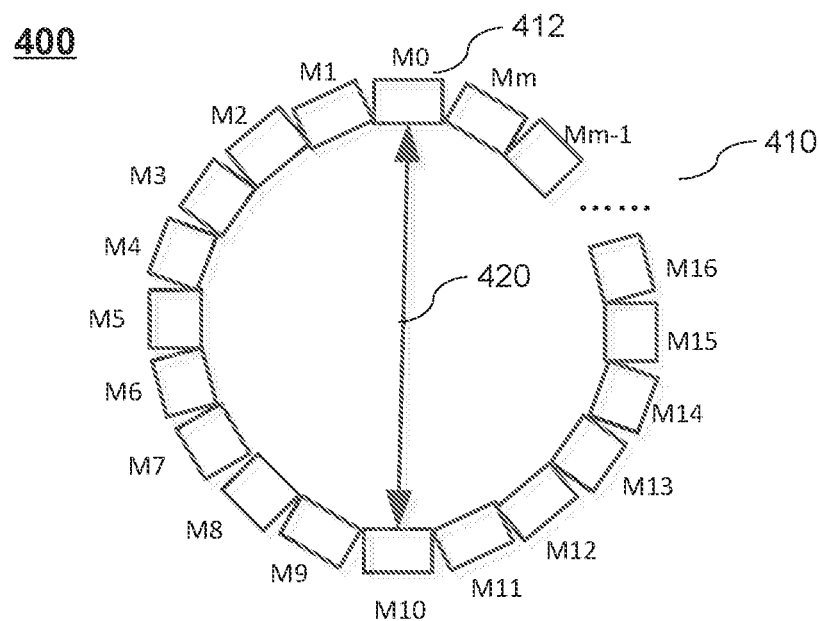
FIG. 4A is a sectional view of a detector module according to some embodiments of the present disclosure.

In some embodiments, the detector module 116 may include one or more detector rings arranged along the detection tunnel of the PET scanner 110, which form a field of view (FOV) of the PET scanner 110. Each detector ring may include a plurality of detector units (e.g., the detector unit 412 as shown in FIG. 4A) arranged along the circumference of the detector ring. In some embodiments, the detection unit may be a scintillation detector unit (e.g., a cesium iodide detector), a gas detector unit, or the like. For example, the detector unit may include a scintillator and a photodetector (e.g., a photomultiplier (PMT)). The scintillator may include a array of scintillation crystals, and the photodetector may be coupled to the scintillator. More descriptions of the detector module 116 may be found elsewhere in the present disclosure (e.g., FIGS. 4A and 4B, and the descriptions thereof).

The network 120 may facilitate exchange of information and/or data. In some embodiments, one or more components of the PET system 100 (e.g., the PET scanner 110, the terminal 130, the processing device 140, or the storage device 150) may send information and/or data to another component(s) in the PET system 100 via the network 120. For example, the processing device 140 may obtain, via the network 120, a cycle difference between a first clock cycle at which a first single event occurs and a second clock cycle at which a second single event occurs. As another example, the processing device 140 may obtain, via the network 120, a first TDC value of the first single event and a second TDC value of the second single event. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the PET system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 130 may remotely operate the PET scanner 110. In some embodiments, the terminal 130 may operate the PET scanner 110 via a wireless connection. In some embodiments, the terminal 130 may receive information and/or instructions inputted by a user, and send the received information and/or instructions to the PET scanner 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may process data obtained from the PET scanner 110, the terminal 130, or the storage device 150. For example, the processing device 140 may determine original coincidence events based on time of occurrence of a plurality of single events. As another example, the processing device 140 may determine random coincidence events by processing the plurality of single events based on cycle offsets of detector units that detect the plurality of single events. The processing device 140 may be a central processing unit (CPU), a digital signal processor (DSP), a system on a chip (SoC), a microcontroller unit (MCU), or the like, or any combination thereof. In some embodiments, the processing device 140 may be a single server or a server group. The server group may be centralized or distributed. In some embodiments, the processing device 140 may be local or remote. For example, the processing device 140 may access information and/or data stored in the PET scanner 110, the terminal 130, and/or the storage device 150 via the network 120. As another example, the processing device 140 may be directly connected to the PET scanner 110, the terminal 130, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the PET system 100 (e.g., the terminal 130, the processing device 140). One or more components of the PET system 100 may access the data or instructions stored in the storage device 150 via the network 120. In some embodiments, the storage device 150 may be directly connected to or communicate with one or more components of the PET system 100 (e.g., the terminal 130, the processing device 140). In some embodiments, the storage device 150 may be part of the processing device 140.

FIG. 2 is a schematic diagram illustrating exemplary hardware and/or software components of a computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the PET scanner 110, the terminal 130, the storage device 150, and/or any other component of the PET system 100. For example, the processor 210 may determine random coincidence events by processing a plurality of single events based on cycle offsets of detector units that detect the plurality of single events. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the PET scanner 110, the terminal 130, the storage device 150, or any other component of the PET system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input or output signals, data, and/or information. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the PET scanner 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
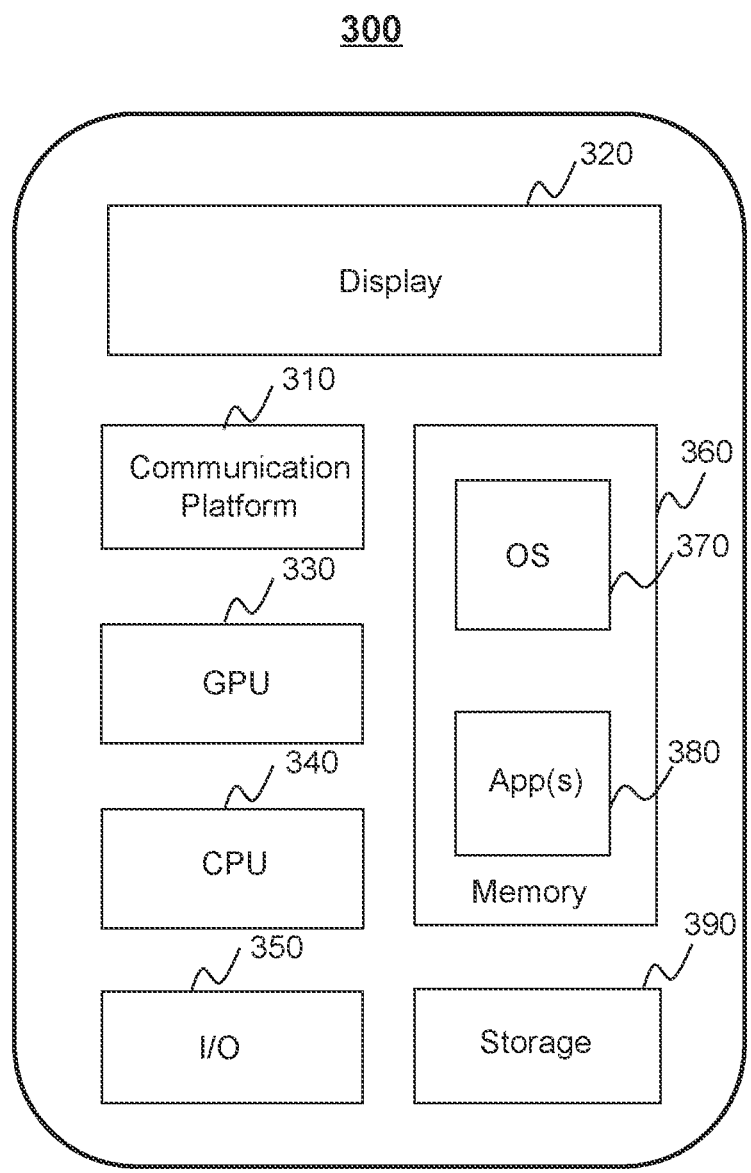
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the PET system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to determine the coincidence events as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4B:
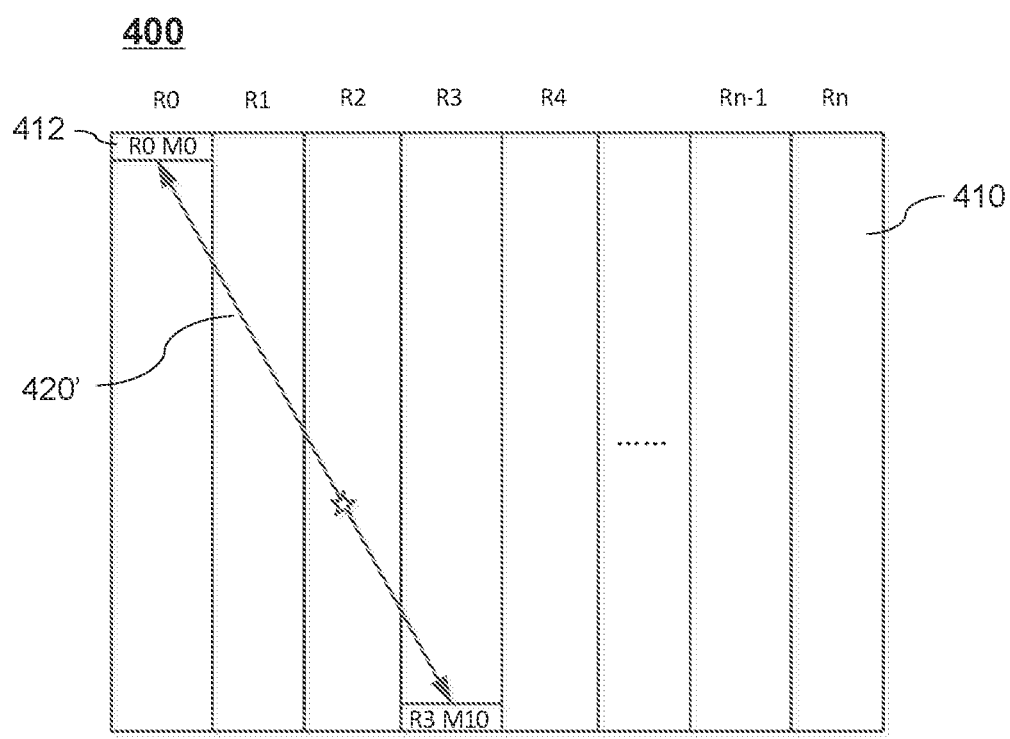
FIG. 4B is a schematic diagram of a detector module according to some embodiments of the present disclosure.

FIG. 4A is a sectional view of a detector module according to some embodiments of the present disclosure. FIG. 4B is a schematic diagram of a detector module according to some embodiments of the present disclosure. In some embodiments, the detector module 400 may include one detector ring (e.g., the detector ring 410 as illustrated in FIG. 4A). The detector ring 410 may include a plurality of detector units 412, such as M0, M1, M2, . . . , Mm (m is an integer greater than 1). Alternatively, the detector module 400 may include a plurality of detector rings (e.g., n detector rings 410 as illustrated in FIG. 4B, wherein n is an integer greater than 1). The detector rings may be labelled as R0, R1, R2, . . . , Rn. The detector units on the detector ring R0 may be labelled as R0M0, R0M1, R0M2, . . . , R0Mm; the detector units on the detector ring R1 may be labelled as R1M0, R1M1, R1M2, . . . , R1Mm; . . . ; and the detector units on the detector ring Rn may be labelled as RnM0, RnM1, RnM2, . . . , RnMm.

In some embodiments, positrons emitted from the tracer (e.g., the radiopharmaceutical) may travel through an object (e.g., the object 118) until they encounter electrons. When a positron and an electron meet, annihilation may occur. The electron-positron annihilation may simultaneously generate two 511 kiloelectron volt (keV) gamma photons traveling in opposite directions. In some embodiments, the two gamma photons may be detected by two detector units on a same detector ring (e.g., detector units M0 and M10 as shown in FIG. 4A), respectively. Alternatively, the two gamma photons may be detected by two detector units on two different detector rings (e.g., detector units R0M0 and R3M10 as shown in FIG. 4B), respectively. The path of the gamma photons is called a line of response (LOR). As shown in FIG. 4A, the LOR 420 connects two detector units within a detector ring. As shown in FIG. 4B, the LOR 420' connects two detector units from different detector rings (e.g., detector rings R0 and R3).

In some embodiments, the detector unit 412 may include a scintillator and a photodetector (e.g., a photomultiplier (PMT)). The scintillator may include a array of scintillation crystals, and the photodetector may be coupled to the scintillator. A gamma photon generated by an electron-positron annihilation may strike the scintillator to produce bursts of visible and invisible light. The visible or invisible light may transmit from the scintillator to the photodetector. The visible or invisible light may be converted to an electrical signal (e.g., an electrical pulse) by the photodetector, and further be transmitted to other components of the PET system 100, such as the processing device 140.

Figure 5:
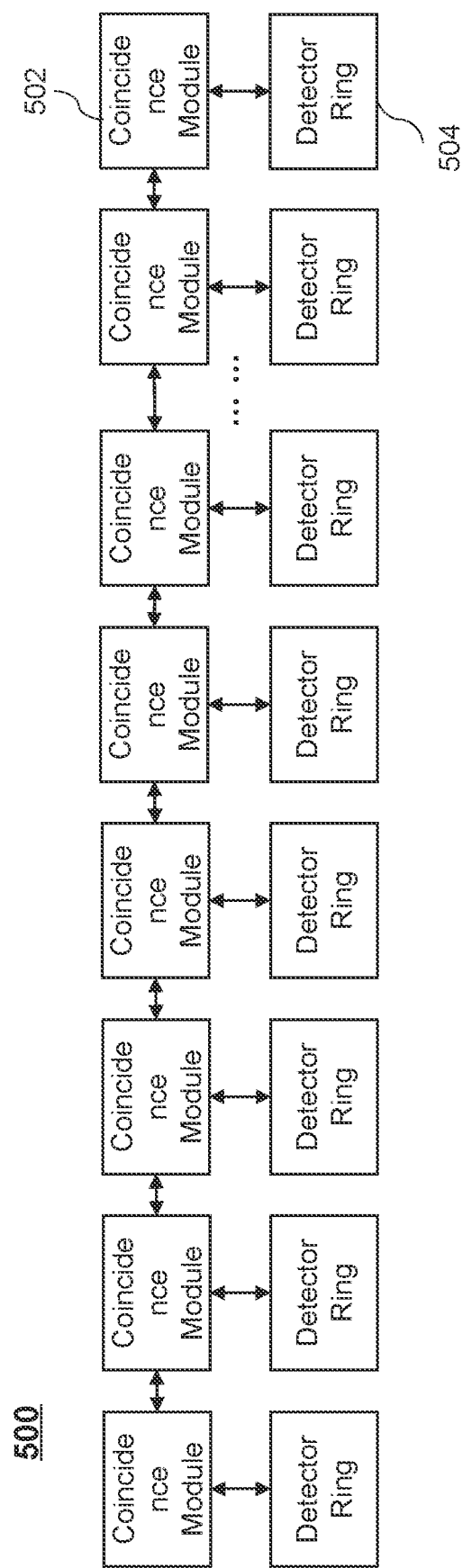
FIG. 5 is a schematic diagram illustrating an exemplary coincidence device according to some embodiments of the present disclosure.

FIG. 5 is a schematic diagram illustrating an exemplary coincidence device (i.e., a device for determining coincidence events) according to some embodiments of the present disclosure. In some embodiments, the coincidence device 500 may be a part of the processing device 140. As shown in FIG. 5, the coincidence device 500 includes one or more coincidence modules 502 and one or more detector rings 504. Each coincidence module 502 may correspond to one of the detector rings 504 and be connected to its corresponding detector ring 504. The number of the detector rings 504 and the number of the coincidence modules 502 may be determined according to actual needs. For example, the coincidence device 500 may include eight coincidence modules 502 and eight detector rings 504. Each detector ring may include a plurality of detector units that are configured to detect data (also referred to as single events) impacting on its corresponding detector units. More descriptions of the detector ring(s) 504 may be found elsewhere in the present disclosure (e.g., FIG. 4 and the descriptions thereof). A coincidence module 502 may receive single events detected by the corresponding detector ring 504 and transmit the single events to an interconnection module (e.g., the interconnection module 612) for storage. The coincidence module(s) 502 may then determine coincidence events based on single events stored in the interconnection module.

In some embodiments, the coincidence events determined by a coincidence module may include first coincidence events (also referred to as local coincidence events) and second incidence events (also referred to as cross coincidence events). In some embodiments, a first coincidence event may include two first single events that corresponding to each other (e.g., single events detected by two detector units on a same detector ring, such as M0 and M10 shown in FIG. 4A). A second coincidence event may include a first single event and a second single event (e.g., single events detected by two detector units on different detector rings, such as R0M0 and R3M10 shown in FIG. 4B). The first single event may be a single event from a detector ring corresponding to the coincidence module. The second single event may be a single event from a detector ring not corresponding to the coincidence module.

Merely by way of example, a coincidence module 502 may obtain single events from the corresponding detector ring (also referred to as the first single events) and determine the first coincidence events (also referred to as the local coincidence events) based on the first single events. The coincidence module 502 may also obtain single events from other detector ring(s) (also referred to as second single events) via the interconnection module, and determine the second coincidence events (also referred to as the cross coincidence events) based on the first single events and the second single events. Details regarding the determination of the (first or second) coincidence events may be found elsewhere in the present disclosure (e.g., FIGS. 8 and 12 and the descriptions thereof).

In some embodiments of the present disclosure, the coincidence modules may simultaneously generate first coincidence events (i.e., local coincidence events) and second coincidence events (i.e., cross coincidence events), which may improve the sensitivity and efficiency of the coincidence device 500. For example, the efficiency of the coincidence device 500 may improve 52 times than a traditional coincidence device. The sensitivity of the coincidence device 500 may improve 40 times than a traditional coincidence device.

Figure 6:
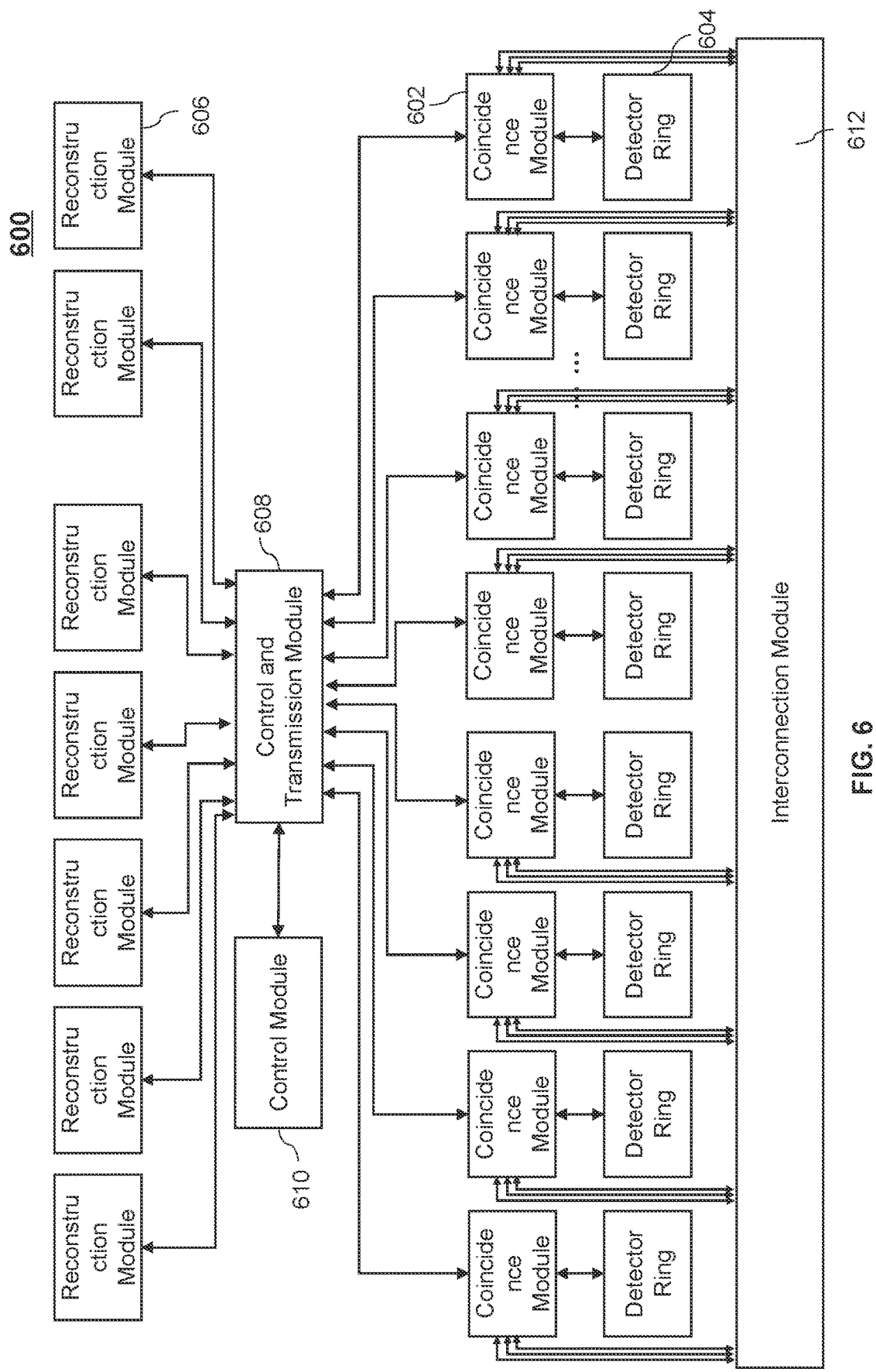
FIG. 6 is a schematic diagram illustrating an exemplary coincidence device according to some embodiments of the present disclosure.

FIG. 6 is a schematic diagram illustrating an exemplary coincidence device according to some embodiments of the present disclosure. In some embodiments, the coincidence device 600 may be a part of the processing device 140. As shown in FIG. 6, the coincidence device 600 may include one or more coincidence modules 602, one or more detector rings 604, at least one reconstruction module 606, a control and transmission module 608, a control module 610, and an interconnection module 612. In some embodiments, the coincidence modules 602 and the detector rings 604 may be the same as the coincidence modules 502 and the detector rings 504, and the descriptions are not repeated here.

The at least one reconstruction module 606 may be connected to the one or more coincidence modules 602 and configured to receive the coincidence events and reconstruct an image (e.g., a PET image) based on the coincidence events. In some embodiments, the reconstruction module 606 may be an image reconstruction machine. The number of the reconstruction modules 606 may be determined according to actual needs. For example, the coincidence device 600 may include only one reconstruction module 606 and configured to receive the coincidence events from all the coincidence modules 602 and reconstruct an image based on the coincidence events. As another example, the number of the reconstruction modules 606 may be the same as the number of the coincidence modules 602. Each reconstruction module 606 may be configured to receive the coincidence events from the corresponding coincidence modules 602 and reconstruct an image based on the coincidence events.

As shown in FIG. 6, the control and transmission module 608 may be disposed between the one or more coincidence modules 602 and the at least one reconstruction module 606. The control and transmission module 608 may be configured to receive the coincidence events and transmit the coincidence events to the at least one reconstruction module 606. In some embodiments, the control module 610 may be connected to the control and transmission module 608 and is configured to transmit an instruction to the control and transmission module 608. For example, the control module 610 may generate an instruction for obtaining coincidence events, and the control and transmission module 608 may obtain the coincidence events from the coincidence modules 602 in response to the instruction. As another example, the control module 610 may generate an instruction for transmitting coincidence events, and the control and transmission module 608 may transmit the obtained coincidence events to the reconstruction module 606 in response to the instruction.

The interconnection module 612 may be connected to the one or more coincidence modules 602. A coincidence module 602 may store the single events detected by the corresponding detector ring 604. The interconnection module 612 may be configured to store the single events detected by all the detector rings 604. A coincidence module 602 may be configured to obtain second single events (i.e., single events detected by other detector rings) from the interconnection module 612. In some embodiments, the interconnection module 612 may include an interconnection matrix. The interconnection matrix may be configured to determine the communication between one or more coincidence modules.

Merely by way of example, Table 1 shows an exemplary interconnection matrix. As shown in Table 1, Unit0, Unit1, . . . , Unit7 each represents a detector unit in a different detector ring, and 0, 1, . . . , 7 refer to the serial number of the detector units. Taking Unit0 as an example for illustration. A coincidence module corresponding to the detector unit Unit0 may receive single events detected by the detector units Unit2, Unit3, Unit4 via the interconnection module 612. Thus, the coincidence module may generate first coincidence events (Unit0-Unit0, or 0-0) based on the single events detected by the detector unit Unit0. The coincidence module may generate second coincidence events (Unit0-Unit2, or 0-2) based on the single events detected by the detector unit Unit0 and the second single events detected by the detector unit Unit2. The coincidence module may generate second coincidence events (Unit0-Unit3, or 0-3) based on the single events detected by the detector unit Unit0 and the second single events detected by the detector unit Unit3. The coincidence module may generate second coincidence events (Unit0-Unit4, or 0-4) based on the single events detected by the detector unit Unit0 and the second single events detected by the detector unit Unit4. In some embodiments, the coincidence module may transmit the single event detected by the detector unit Unit0 to the detector unit Unit1 via the interconnection module 612. It should be noted that the interconnection matrix is merely for illustration purposes and is not intended to limit the scope of the present disclosure. In some embodiments, the interconnection matrix may have other modes.

TABLE 1 an exemplary interconnection matrix

| | Input from | Output to | Coincidence |
|---|---|---|---|
| Unit 0 | 2, 3, 4 | 1 | 0-0, 0-2, 0-3, 0-4 |
| Unit 1 | 0, 3, 4 | 2, 5 | 1-1, 1-0, 1-3, 1-4 |
| Unit 2 | 1, 4, 6 | 0, 3, 5 | 2-2, 2-1, 2-4, 2-6 |
| Unit 3 | 2, 6, 7 | 0, 1, 4, 5 | 3-3, 3-2, 3-6, 3-7 |
| Unit 4 | 3, 5, 6 | 0, 1, 2, 7 | 4-4, 4-3, 4-5, 4-6 |
| Unit 5 | 1, 2, 3 | 4, 6, 7 | 5-5, 5-1, 5-2, 5-3 |
| Unit 6 | 5, 7 | 2, 3, 4 | 6-6, 6-5, 6-7 |
| Unit 7 | 4, 5 | 3, 6 | 7-7, 7-4, 7-5 |

Figure 7:
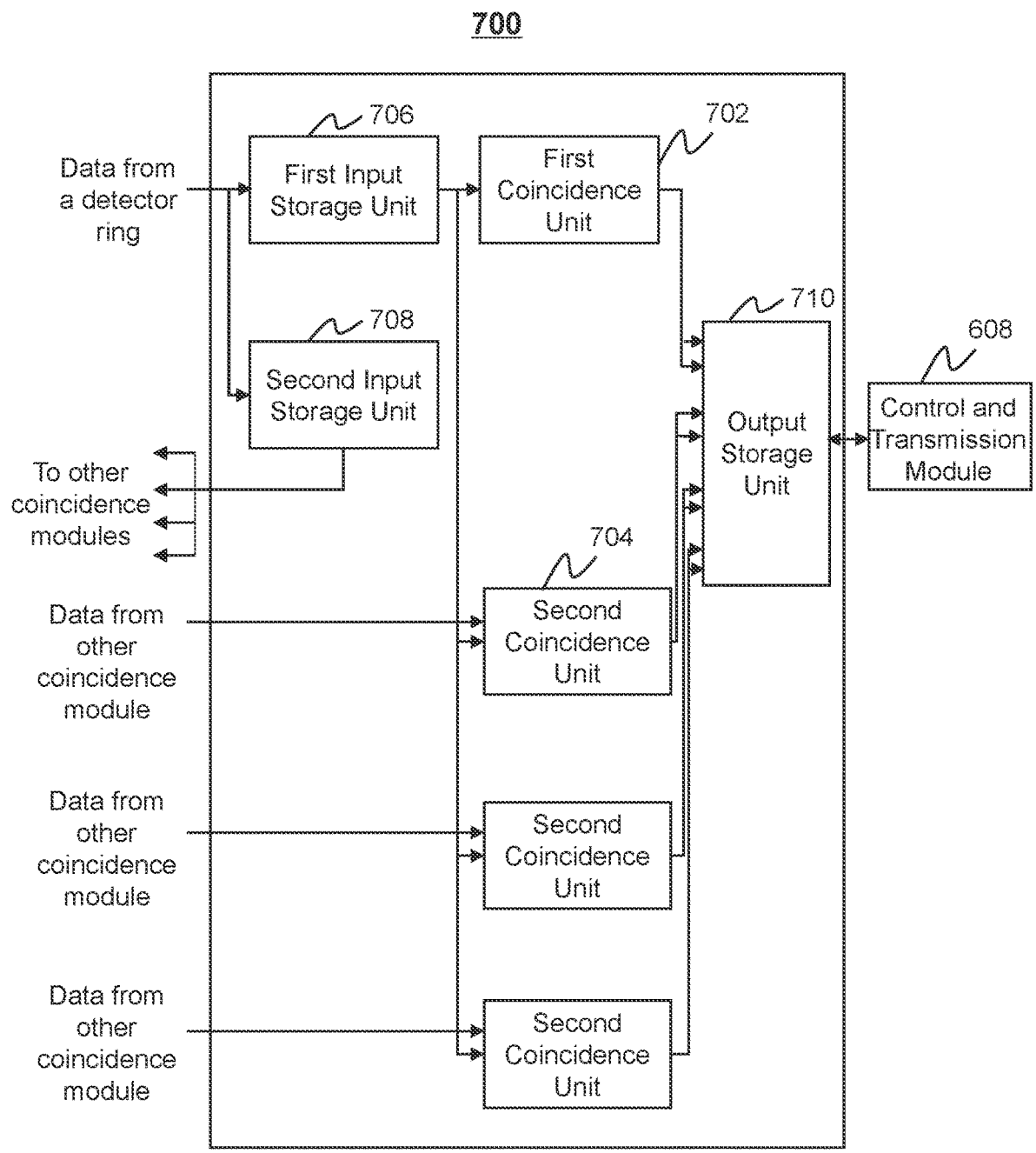
FIG. 7 is a schematic diagram illustrating an exemplary coincidence module according to some embodiments of the present disclosure.

FIG. 7 is a schematic diagram illustrating an exemplary coincidence module according to some embodiments of the present disclosure. The coincidence module 700 may be an example of the coincidence module 502 or coincidence module 602. The coincidence module 700 may include a first coincidence unit (also referred to as local coincidence unit) 702, one or more second coincidence units (also referred to as cross coincidence unit) 704, a first input storage device 706, a second input storage device 708, and an output storage device 710.

The first input storage device 706 may be connected to the first coincidence unit 702 and the second coincidence unit(s) 704. The first input storage device 706 may be configured to receive data (i.e., single events) from the detector ring corresponding to the coincidence module 700 and transmit the data (i.e., the single events) to the first coincidence unit 702 and the second coincidence unit(s) 704. The second input storage device 708 may be connected to an interconnection module (e.g., the interconnection module 612 in FIG. 6). The second input storage device 708 may be configured to receive the data (i.e., single events) from the detector ring corresponding to the coincidence module 700 and transmit the data (i.e., the single events) to the interconnection module (e.g., the interconnection module 612). Other coincidence module(s) may obtain the single events via the interconnection module (e.g., the interconnection module 612).

In some embodiments, the first coincidence unit 702 may be configured to obtain multiple first single events (single events from the corresponding detector ring) and determine multiple first coincidence events based on the multiple first single events. The first coincidence unit 702 may transmit the first coincidence events to the output storage unit 710. In some embodiments, the coincidence module 700 may include only one second coincidence unit 704. The second coincidence unit 704 may obtain the multiple first single events. The second coincidence unit 704 may also obtain multiple second single events (single events from one or more other coincidence modules via the interconnection module (e.g., the interconnection module 612)). The second coincidence unit 704 may then determine multiple second coincidence events based on the multiple first single events and the multiple second single events. The second coincidence unit 704 may transmit the second coincidence events to the output storage unit 710. Alternatively or additionally, the coincidence module 700 may include a plurality of second coincidence units 704, each of which corresponds to one other coincidence module. Each coincidence unit 704 may obtain the multiple first single events. Each coincidence unit 704 may also obtain multiple second coincidence events from its corresponding coincidence module via the interconnection module (e.g., the interconnection module 612). Each second coincidence unit 704 may determine second coincidence events based on the first single events and the obtained second single events. Each second coincidence unit 704 may transmit the second coincidence events to the output storage unit 710. In some embodiments, the output storage unit 710 may be connected to the control and transmission module 608, and configured to transmit the first coincidence events and the second coincidence events to the control and transmission module 608. The control and transmission module 608 may transmit the first coincidence events and the second coincidence events to the reconstruction module 606 for reconstructing an image.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the coincidence module 700 may include a first output storage unit and a second output storage unit. The first output storage unit may be configured to store the first coincidence events, and the second output storage unit may be configured to store the second coincidence events.

Figure 8:
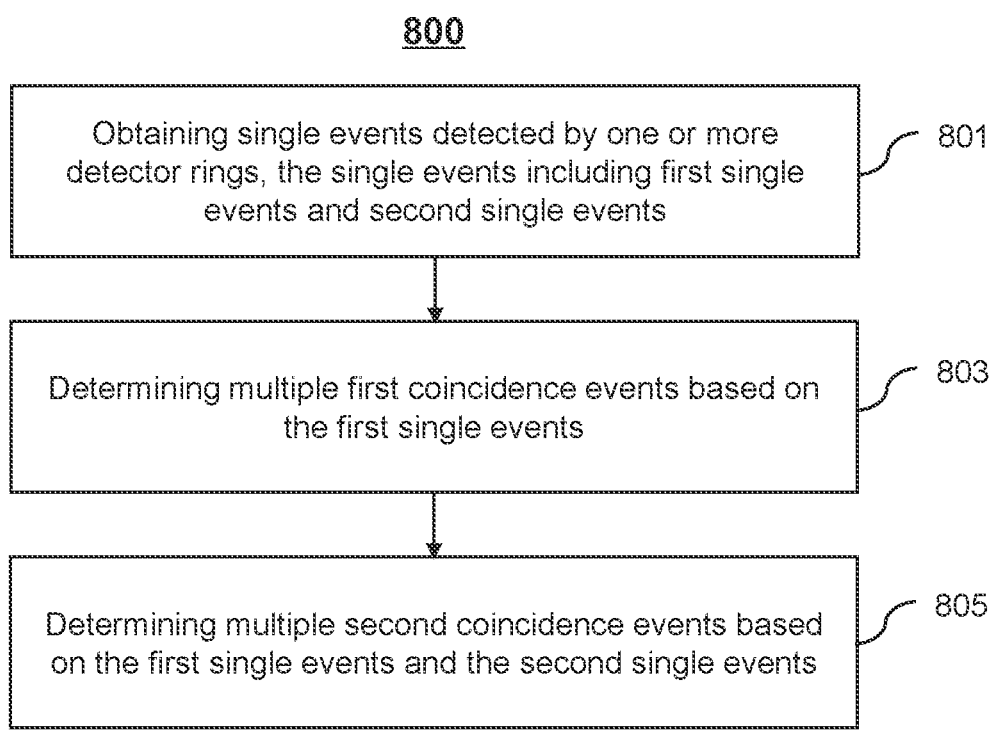
FIG. 8 is a flowchart illustrating an exemplary process for determining coincidence events according to some embodiments of the present disclosure.

FIG. 8 is a flowchart illustrating an exemplary process for determining coincidence events according to some embodiments of the present disclosure. However, one of ordinary skill in the art would understand that the process 800 may also be performed by other entities. In some embodiments, one or more operations of process 800 may be implemented in the PET system 100 illustrated in FIG. 1. For example, the process 800 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, the coincidence module 700 as illustrated in FIG. 7, or the like). As another example, a portion of the process 800 may be implemented on the PET scanner 110. The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 801, a coincidence module (e.g., the coincidence module 700) may obtain single events detected by one or more detector rings. In some embodiments, the single events may include first single events and second single events. The first single events may be single events detected by a detector ring corresponding to the coincidence module 700. The second single events may be single events detected by one or more detector rings not corresponding to the coincidence module 700. In some embodiments, the first coincidence unit 702 may obtain the first single events from the detector ring corresponding to the coincidence module 700. The second coincidence unit 704 may obtain the second single events from one or more other coincidence modules via the interconnection module 612.

In 803, the coincidence module (e.g., the first coincidence unit 702 of the coincidence module 700) may determine multiple first coincidence events based on the first single events. In 805, the coincidence module (e.g., the second coincidence unit 704 of the coincidence module 700) may determine multiple second coincidence events based on the first single events and the second single events. In some embodiments, the first coincidence events and/or second coincidence events may be original coincidence events including true coincidence events and random coincidence events. Alternatively, the first coincidence events and/or second coincidence events may be the true coincidence events. In some embodiments, the determination of the first coincidence events and/or the second coincidence events may be found elsewhere in the present disclosure (e.g., FIGS. 12-16 and the descriptions thereof).

It should be noted that the above description of the process 800 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, operations 803 and 805 may be performed simultaneously. Alternatively, operation 805 may be performed before operation 803.

In some embodiments, the present disclosure provides a PET system. The PET system may include a coincidence device (e.g., the coincidence devices 500-600), a gantry, a table, and a console computer (also referred to as a processor). In some embodiments, the coincidence device may be connected with the gantry. The console computer may be connected with the gantry. The gantry may surround the table. In some embodiments, the coincidence device may include one or more detector rings and one or more coincidence modules. Each coincidence module may correspond to each of the one or more detector rings, respectively. In some embodiments, the one or more detector rings may be arranged along a detection tunnel of the gantry. Each detector ring may include a plurality of detector units arranged along a circumference of the detector ring.

FIGS. 9A-9D show four kinds of coincidence events according to some embodiments of the present disclosure. As shown in FIGS. 9A-9D, a detector ring 930 surrounds an object 910 (e.g., a patient). The detector ring 930 includes a plurality of detector units, such as M0, M1, M2, . . . , M19. The detector unit(s) may be configured to detect γ-rays generated by electron-positron annihilation.

Figure 9A:
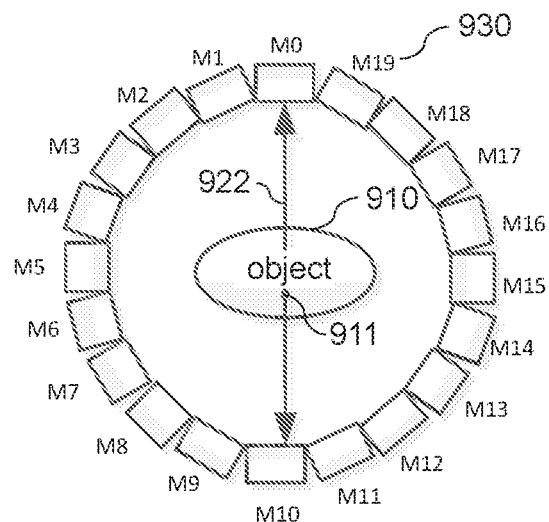
FIGS. 9A-9D show four kinds of coincidence events according to some embodiments of the present disclosure.

As shown in FIG. 9A, a black dot 911 within the object 910 indicates a positron annihilation position. Two γ-rays generated by the annihilation event may be detected at an opposed pair of detector units M0 and M10 of the detector ring 930, which is called a true coincidence event. In the true coincidence event, the data associated with the detected γ-rays may be used to determine an actual LOR 922 associated with the annihilation event.

Figure 9B:
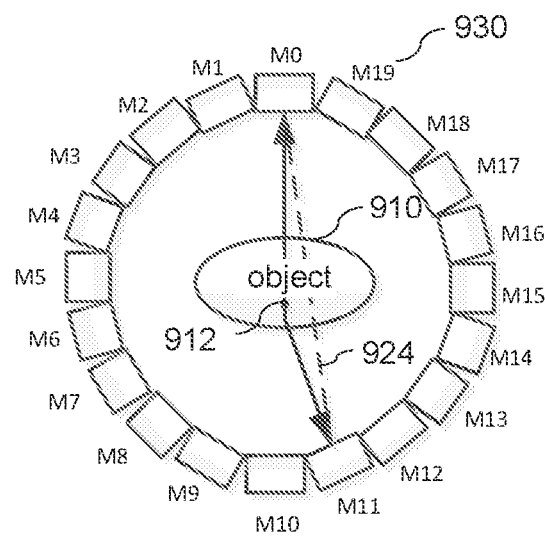

As shown in FIG. 9B, a black dot 912 within the object 910 indicates a positron annihilation position. Compton scatter may occur in one or both of the g-rays generated by the annihilation event, causing the motion trajectory of the γ-rays to shift, which is called a scattered event. As shown in FIG. 9B, the two γ-rays are detected by detector units M0 and M11 other than the detector units M0 and M10. Accordingly, in the scattered event, the data associated with the detected γ-rays may correspond to a shift LOR 924, which will be attributed to a shifted or false annihilation event position, thereby degrading the resolution and sensitivity of the PET system.

Figure 9C:
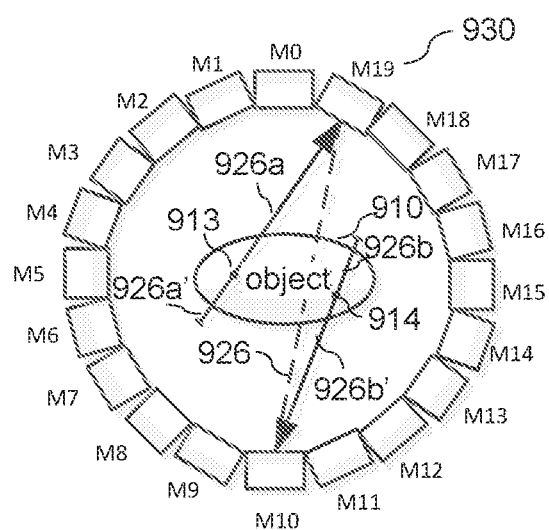

As shown in FIG. 9C, black dots 913 and 914 within the object 910 indicates two positron annihilation positions. The γ-rays 926a' and 926b from each of the two annihilation events are prevented to reach the detector ring 930, and thus, the detector units of the detector ring 930 cannot detect the γ-rays 926a' and 926b. A random event occurs when the remaining γ-rays 926a and 926b' from each of the two annihilation events are detected at an opposed pair of detector units M19 and M10 of the detector ring 930. Accordingly, in the random event, the data associated with the detected γ-rays may correspond to a false LOR 926, which will be attributed to a shifted or false annihilation event position, thereby degrading the resolution and sensitivity of the PET system.

Figure 9D:
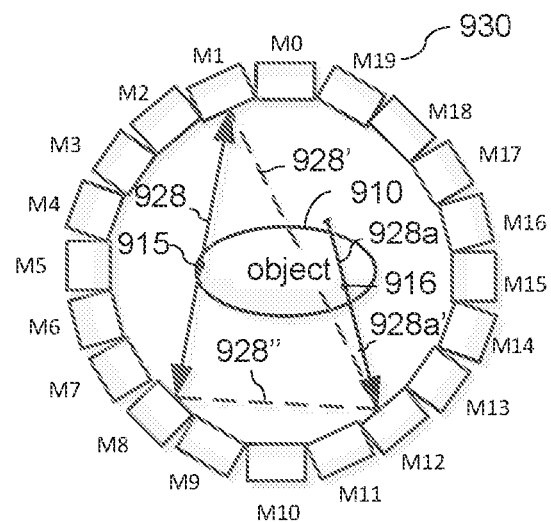

As shown in FIG. 9D, black dots 915 and 916 within the object 910 indicates two positron annihilation positions. Two γ-rays generated at the annihilation position 915 may be detected at an opposed pair of detector units M1 and M8 of the detector ring 930. A γ-ray 928a generated at the annihilation position 916 is prevented to reach the detector ring, and thus, the detector ring 930 cannot detect the γ-ray 928a. The remaining γ-ray 928b generated at the annihilation position 916 is detected at detector unit M12 of the detector ring 930. In this case, the data associated with the γ-rays detected by detector units M1 and M8 may correspond to a first LOR 928. The data associated with the γ-rays detected by detector units M1 and M12 may correspond to a second LOR 928'. The data associated with the g-rays detected by detector units M8 and M12 may correspond to a third LOR 928". In this case, only the first LOR 928 corresponds to a true annihilation position. Thus, the second LOR 928' and the third LOR 928" will be attributed to a false annihilation event position, thereby degrading the resolution and sensitivity of the PET system.

In PET imaging, the coincidence device (e.g., the coincidence devices 500-700) may determine two single events detected by detector units as a coincidence events if they occur within a specified coincidence window width. Thus, the coincidence events may include true coincidence events (as shown in FIG. 9A), scattered events (as shown in FIG. 9B), random events (as shown in FIGS. 9C-9D), etc. The existence of the scattered events and random events may degrade the performance of the PET system 100. Thus, the scattered events and random events may need to be reduced or eliminated to improve the performance of the PET system 100.

Figure 10:
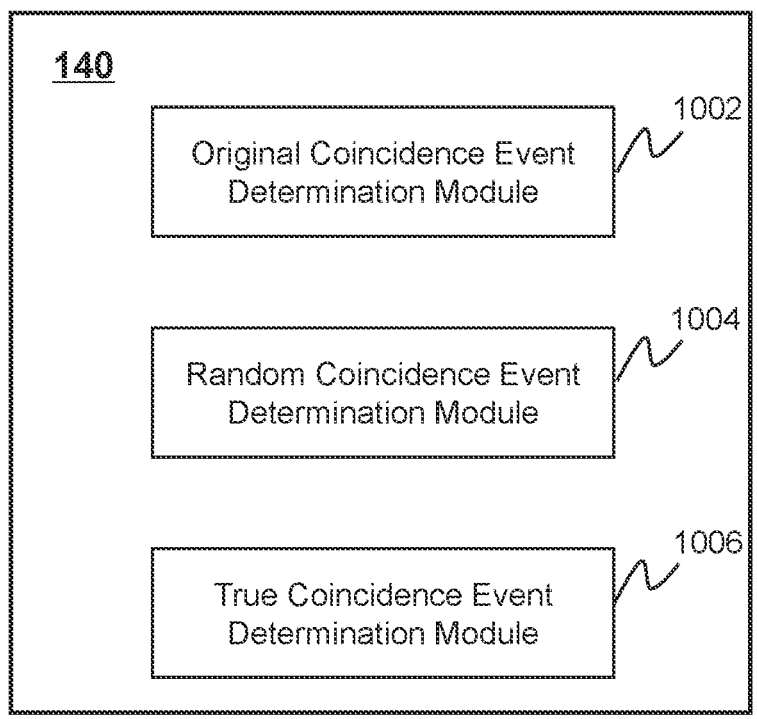
FIG. 10 is a block diagram illustrating an exemplary processing device according to some embodiments of the present disclosure.

FIG. 10 is a block diagram illustrating an exemplary processing device according to some embodiments of the present disclosure. The processing device 140 may be implemented on the computing device 200 (e.g., the processor 210 as illustrated in FIG. 2 or the CPU 340 as illustrated in FIG. 3). The processing device 140 may include an original coincidence event determination module 1002, a random coincidence event determination module 1004, and a true coincidence event determination module 1006.

The original coincidence event determination module 1002 may be configured to determine original coincidence events based on time of occurrence of a plurality of single events. For example, the original coincidence event determination module 1002 may obtain the time of occurrence of a first single event and the time of occurrence of a second single event, and determine a time difference between the time of occurrence of the first single event and the time of occurrence of the second single event. The original coincidence event determination module 1002 may determine whether the time difference is less than a predetermined coincidence window width. In response to a determination that the time difference is less than the predetermined coincidence window width, the original coincidence event determination module 1002 may determine the first single event and the second single event as an original coincidence event.

The random coincidence event determination module 1004 may be configured to determine random coincidence events. The random coincidence events may refer to false coincidence events in the original coincidence events. In some embodiments, the random coincidence event determination module 1004 may determine the random coincidence events by processing the plurality of single events based on cycle offsets of detector units that detect the plurality of single events. For example, for each single event of the plurality of single events, the random coincidence event determination module 1004 obtain a cycle offset of a detector unit that detect the single event. The random coincidence event determination module 1004 may adjust the time of occurrence of the single event by increasing the cycle offset to the time of occurrence of the single event. The random coincidence event determination module 1004 may then determine the random coincidence events based on the adjustment of the time of occurrence of each single event. In some embodiments, the cycle offsets of different detector units may be different. A difference of any two cycle offsets may be greater than the predetermined coincidence window width. Thus, after the adjustment by the cycle offsets, the original coincidence events must be converted into non-coincidence events. A portion of original non-coincidence events may be converted into coincidence events. After the adjustment by the cycle offsets, the random coincidence events may be identified from the original coincidence events. More descriptions of the determination of the random coincidence events may be found elsewhere in the present disclosure (e.g., operation 1203 of process 1200, and the descriptions thereof).

The true coincidence event determination module 1006 may be configured to determine true coincidence events based on the original coincidence events and the random coincidence events. In some embodiments, the original coincidence events may include true coincidence events and random coincidence events. The true coincidence event determination module 1006 may determine the true coincidence events by removing the random coincidence events from the original coincidence events.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 10). The storage module may be configured to store data generated by the processing device 140.

Figure 11:
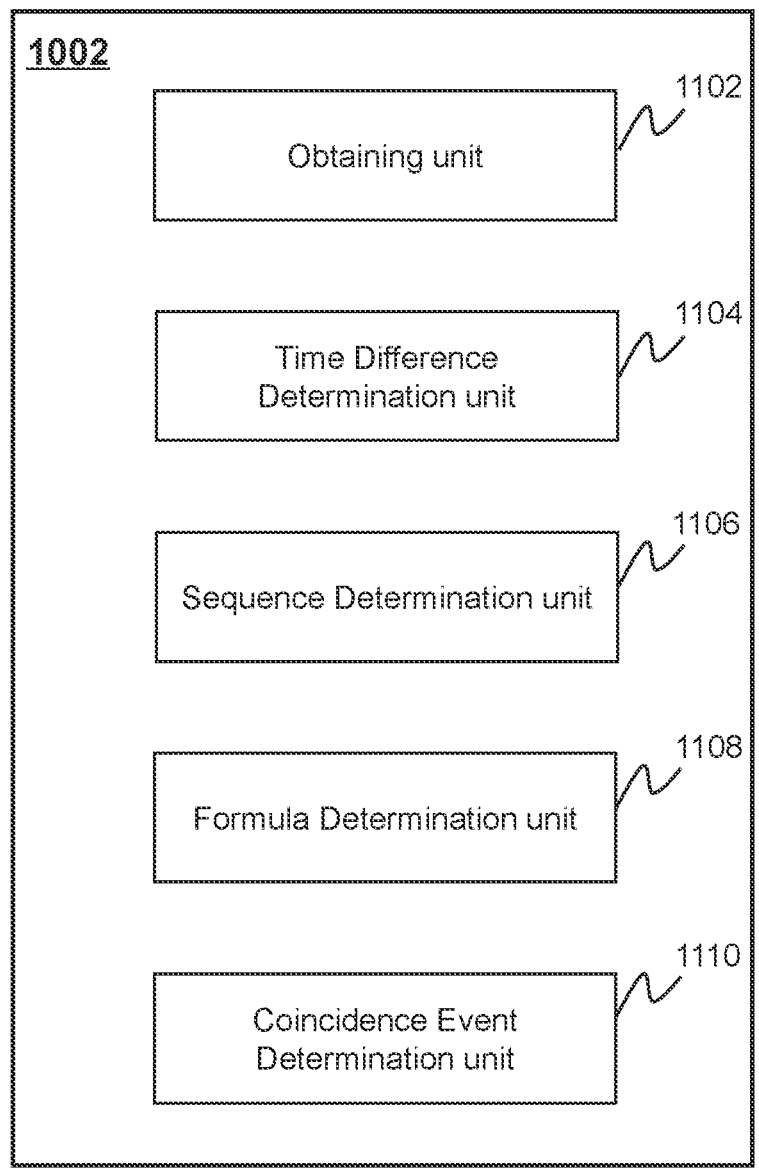
FIG. 11 is a block diagram illustrating an exemplary original coincidence event determination module according to some embodiments of the present disclosure.

FIG. 11 is a block diagram illustrating an exemplary original coincidence event determination module according to some embodiments of the present disclosure. The original coincidence event determination module 1002 may include an obtaining unit 1102, a time difference determination unit 1104, a sequence determination unit 1106, a formula determination unit 1108, and a coincidence event determination unit 1110.

The obtaining unit 1102 may be configured to obtain information and/or data related to the PET system 100. In some embodiments, the obtaining unit 1102 may obtain a clock cycle at which a single event occurs. The clock cycles of different single events may be used to determine a cycle difference. For example, the obtaining unit 1102 may obtain a first clock cycle at which a first single event occurs and a second clock cycle at which a second single event occurs. The obtaining unit 1102 may determine a cycle difference between the first clock cycle and the second clock cycle. In some embodiments, the first clock cycle and the second clock cycle may be in the same clock cycle or difference clock cycles. In some embodiments, the obtaining unit 1102 may directly obtain the cycle difference between the first clock cycle and the second clock cycle from other units of the processing device 140 (e.g., a cycle difference determination unit). In some embodiments, the obtaining unit 1102 may obtain a first time-to-digital converter (TDC) value of the first single event and a second TDC value of the second single event. The first TDC value, the second TDC value, and the cycle difference may be used to determine a time difference between the first single event and the second single event.

The time difference determination unit 1104 may be configured to determine a time difference between the time of occurrence of two single events (e.g., the first single event and the second single event). In some embodiments, if the cycle difference is equal to 0 (i.e., the first clock cycle and the second clock cycle are in the same clock cycle), the time difference between the time occurrence of the first single event and the time of occurrence of the second single event may be an absolute value of the difference between the first TDC value and the second TDC value. Alternatively or additionally, if the cycle difference is non-zero (i.e., the first clock cycle and the second clock cycle are in different clock cycles), the time difference determination unit 1104 may determine the time difference according to a time difference determination formula. The time difference determination formula may be determined by the formula determination unit 1108.

The sequence determination unit 1106 may be configured to determine a sequence that the first single event and the second single event occurs. In some embodiments, the sequence determination unit 1106 may determine the sequence based on the cycle difference. If the cycle difference is greater than 0, the first single event may occur before the second single event. If the cycle difference is less than 0, the first single event may lag behind the second single event. Alternatively or additionally, if the cycle difference is equal to 0, the sequence determination unit 1106 may determine the sequence based on the first TDC value and the second TDC value. For example, if the first TDC value is greater than the second TDC value, the first single event may occur before the second single event. As another example, if the first TDC value is less than the second TDC value, the first single event may lag behind the second single event.

The formula determination unit 1108 may be configured to determine a time difference determination formula based on the sequence. More descriptions of the determination of the time difference determination formula may be found elsewhere in the present disclosure (e.g., operation 1505 of the process 1500 and the descriptions thereof).

The coincidence event determination unit 1110 may be configured to determine whether two single events are the coincidence event. For example, if the time difference between the time occurrence of the first single event and the time of occurrence of the second single event is less than a predetermined coincidence window width, the coincidence event determination unit 1110 may determine the first single event and the second single event as the coincidence event. The predetermined coincidence window width may be a default value or an empirical value related to the PET system 100. For example, the predetermined coincidence window width may be 10 ns, 15 ns, 20 ns, 25 ns, 30 ns, etc.

The modules in the original coincidence event determination module 1002 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the original coincidence event determination module 1002 may also include a coincidence event output unit, which is configured to output one or more coincidence events to other components of the PET system 100 (e.g., the storage device 150).

Figure 12:
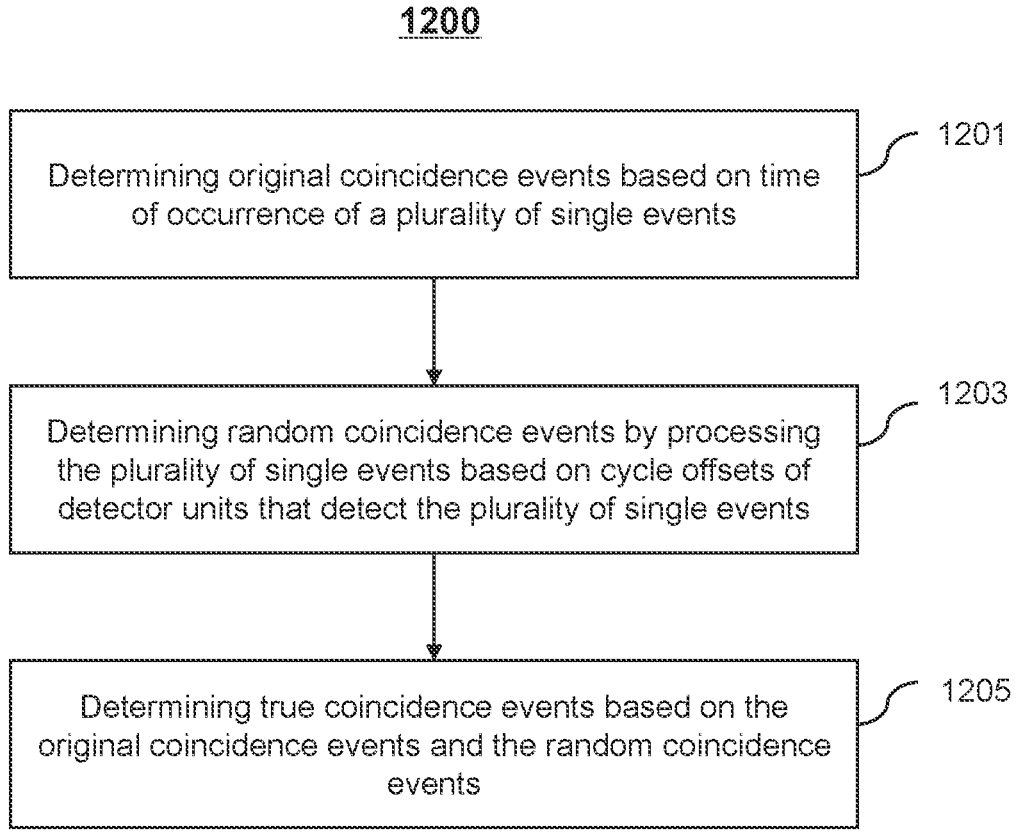
FIG. 12 is a flowchart illustrating an exemplary process for determining true coincidence events according to some embodiments of the present disclosure.

FIG. 12 is a flowchart illustrating an exemplary process for determining true coincidence events according to some embodiments of the present disclosure. In some embodiments, the process 1200 can be applied for a detector module having one or more detector rings. In some embodiments, one or more operations of process 1200 may be implemented in the PET system 100 illustrated in FIG. 1. For example, the process 1200 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, the coincidence devices 500-600, one or more modules of the processing device 140 as illustrated in FIG. 10, or the like). As another example, a portion of the process 1200 may be implemented on the PET scanner 110. The operations of the illustrated process presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting.

In 1201, the processing device 140 (e.g., the original coincidence event determination module 1002) may determine original coincidence events based on time of occurrence of a plurality of single events. In some embodiments, the PET module may include a detector ring, and the single events may be detected by the detector ring. Alternatively, the PET module may include two or more detector rings, and the single events may be detected by the two or more detector rings. The processing device 140 may determine the original coincidence events based on the single events from a same detector ring or from different detector rings.

In some embodiments, the processing device 140 may determine the original coincidence events based on a time difference between the time of occurrence of the single events. For example, the processing device 140 may determine whether a time difference between a time of occurrence of a first single event and a time of occurrence of a second single event is less than a predetermined coincidence window width. In response to a determination that the time difference is less than the predetermined coincidence window width, the processing device 140 may determine the first single event and the second single event as an original coincidence event. In some embodiments, the time of occurrence of a single event (e.g., the first or second single event) may be determined based on a clock cycle of the single event and a time-to-digital converter (TDC) value of the single event. The predetermined coincidence window width may be a default value or an empirical value related to the PET system 100. In some embodiments, the predetermined coincidence window width may be set according to a default setting of the PET system 100, or preset by a user. For example, for the single events from a same detector ring, the processing device 140 may preset a first coincidence window width. For the single events from different detector rings, the processing device 140 may preset a second coincidence window width. In some embodiments, the first coincidence window width may be less than the second coincidence window width. More description of the original coincidence events may be found elsewhere in the present disclosure (e.g., FIG. 14 and the descriptions thereof).

In 1203, the processing device 140 (e.g., the random coincidence event determination module 1004) may determine random coincidence events by processing the plurality of single events based on cycle offsets of detector units that detect the plurality of single events. The random coincidence events may refer to false coincidence events in the original coincidence events.

In some embodiments, the plurality of single events may be detected by one or more detector rings. Each detector ring may include a plurality of detector units. In some embodiments, for each single event of the plurality of single events, the processing device 140 may obtain a cycle offset of a detector unit that detect the single event. The processing device 140 may adjust the time of occurrence of the single event by increasing the cycle offset to the time of occurrence of the single event. The processing device 140 may then determine the random coincidence events based on the adjustment of the time of occurrence of each single event. Merely by way of example, the processing device 140 may adjust the time of occurrence of a third single event by increasing the corresponding cycle offset to the time of occurrence of the third single event. The processing device 140 may adjust the time of occurrence of a fourth single event by increasing the corresponding cycle offset to the time of occurrence of the fourth single event. The processing device 140 may determine whether a time difference between an adjusted time of occurrence of the third single event and an adjusted time of occurrence of the fourth single event is less than the predetermined coincidence window width. In response to the determination that the time difference is less than the predetermined coincidence window width, the processing device 140 may determine the third single event and the fourth event as a random coincidence event. It should be noted that the above description of the adjustment manner is merely for illustration purposes, and is not intended to limit the scope of the present disclosure. In some embodiments, the processing device 140 may adjust the time of occurrence of the single event by decreasing the cycle offset to the time of occurrence of the single event.

Figure 18A:
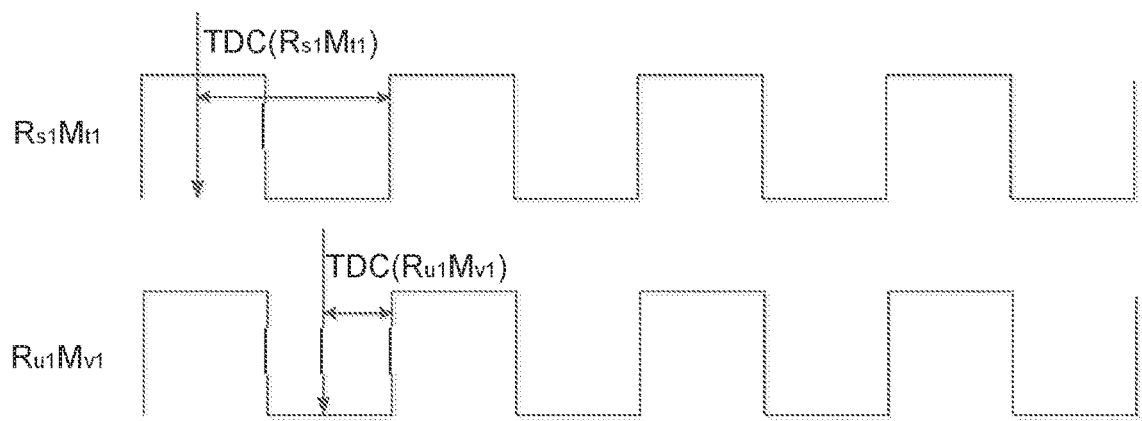
FIGS. 18A-18D are schematic diagrams illustrating the adjustment of single events according to some embodiments of the present disclosure.
Figure 18B:
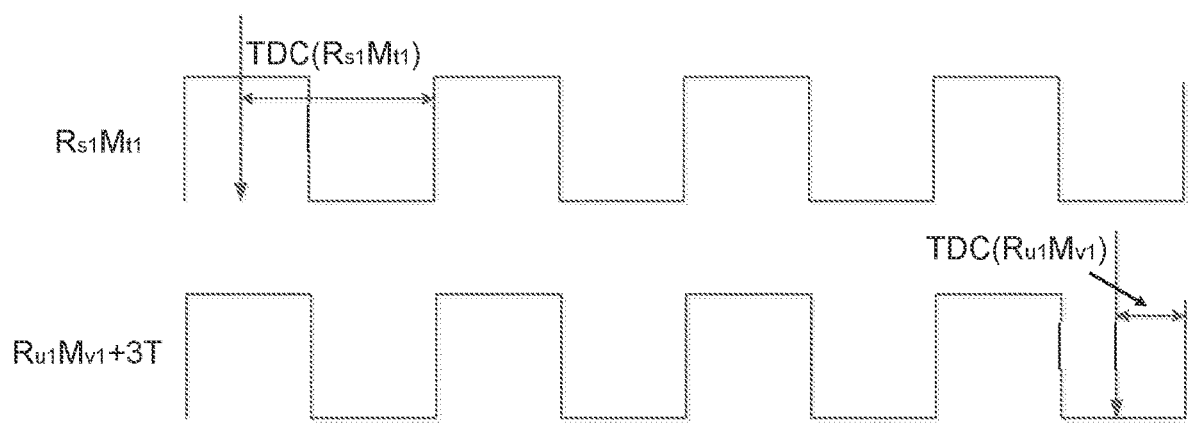
Figure 18C:
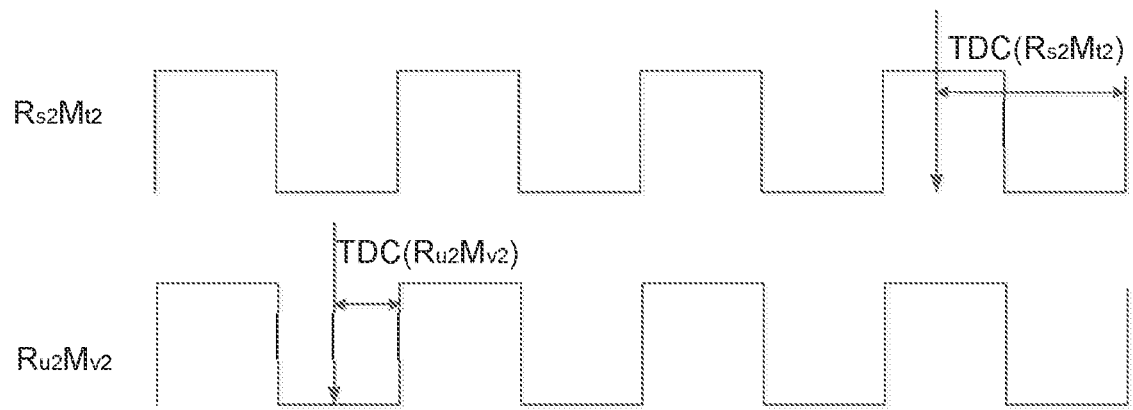
Figure 18D:
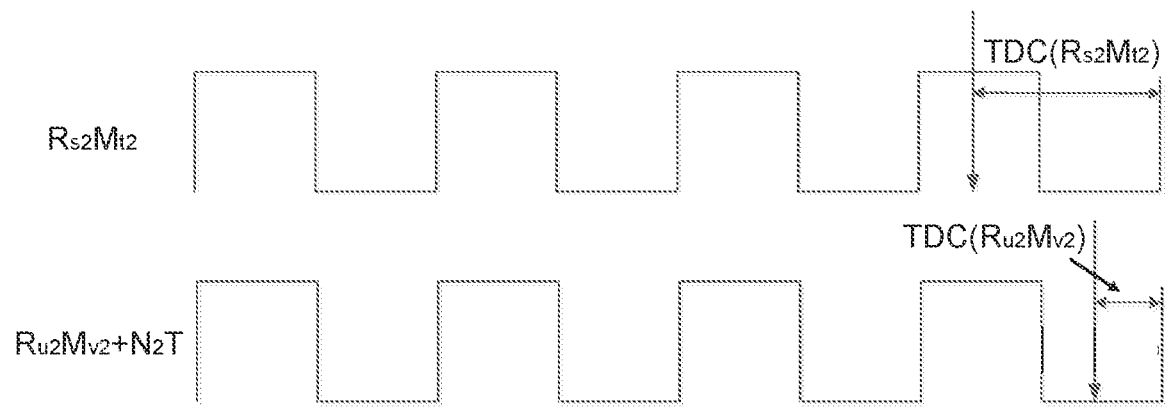

In some embodiments, each detector unit may correspond to a cycle offset. The cycle offsets of different detector units may be different. A difference of any two cycle offsets may be greater than the predetermined coincidence window width. In this case, after the time of occurrence of single event(s) is adjusted by its corresponding cycle offsets, the original coincidence events must be converted into non-coincidence events (as shown in FIGS. 18A-18B). A portion of original non-coincidence events may be converted into coincidence events (as shown in FIGS. 18C-18D). After the adjustment by the cycle offsets, the random coincidence events may be identified from the original coincidence events. Besides, the generation of random coincidence events based on the cycle offset can be applied to detector units from multiple detector rings (i.e., cross-detector units) or detector units from a single detector ring (i.e., inner-detector units).

In some embodiments, the cycle offset of a detector unit may be an integer multiple of a clock cycle. The clock cycle may be related to the number of detector units. Merely by way of example, the cycle offset of a detector unit may include a coded value of the detector unit and a parameter value of the detector unit. The coded values of different detector units may be different. Accordingly, the cycle offset of different detector units may be different. In some embodiments, the coded value of the detector unit(s) may be preset to ensure the coded values of different detector units are different. Merely by way of example, the coded value of a detector unit may be determined according to Equation (1) as below:

$$C=m*X+Y, \quad (1)$$

wherein C refers to the coded value of the detector unit; m refers to the number of detector units of a detector ring; X refers to the serial number of detector ring; Y refers to the serial number of detector unit. It should be noted that the coded values may be preset according to other algorithms as long as the coded values of different detector units are different.

The parameter value of different units may be the same or different. The parameter value of the detector unit may be an integer multiple of the clock cycle and be greater than the predetermined coincidence window width. For example, the parameter value of a detector unit may be determined according to Equation (2) as below:

$$P=K*T, \quad (2)$$

wherein P refers to the parameter value of the detector unit; K is a coefficient and an integer; T refers to the clock cycle. In some embodiments, the parameter value may be greater than the predetermined coincidence window width. For example, $P=K*T>2*Twindow$. Twindow refers to the predetermined coincidence window width.

Accordingly, the cycle offset of a detector unit may be determined according to Equation (3) as below:

$$D=C*P=(m*X+Y)*K*T, \quad (3)$$

wherein D refers to the cycle offset of the detector unit.

In 1205, the processing device 140 (e.g., the true coincidence event determination module 1006) may determine true coincidence events based on the original coincidence events and the random coincidence events. In some embodiments, the original coincidence events may include true coincidence events and random coincidence events. The processing device 140 may determine the true coincidence events by removing the random coincidence events from the original coincidence events.

In some embodiments of the present disclosure, the processing device 140 may determine the original coincidence events from the plurality of single events, and determine the random coincidence events by processing the plurality of single events based on cycle offsets of detector units that detect the plurality of single events. The random coincidence events may be false coincidence events in the original coincidence events. The processing device 140 may further determine the true coincidence events based on the original coincidence events and the random coincidence events, which may improve the resolution and sensitivity of the PET system. Besides, the generation of random coincidence events based on the cycle offset can be applied to detector units from multiple detector rings (i.e., cross-detector units) or detector units from a single detector ring (i.e., inner-detector units).

It should be noted that the above description of the process 1200 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, operations 1201 and 1203 may be performed simultaneously. Alternatively, operation 1203 may be performed before operation 1201.

In some embodiments, the present disclosure also provides a computer-readable storage medium including computer executable instructions. When the computer executable instructions are executed by a processor (e.g., the processing device 140), the computer executable instructions may direct the processor to perform acts of: determining original coincidence events based on time of occurrence of a plurality of single events; determining random coincidence events by processing the plurality of single events based on cycle offsets of detector units that detect the plurality of single events, wherein a difference of any two cycle offsets is greater than a predetermined coincidence window width; and determining the true coincidence events based on the original coincidence events and the random coincidence events.

Figure 13:
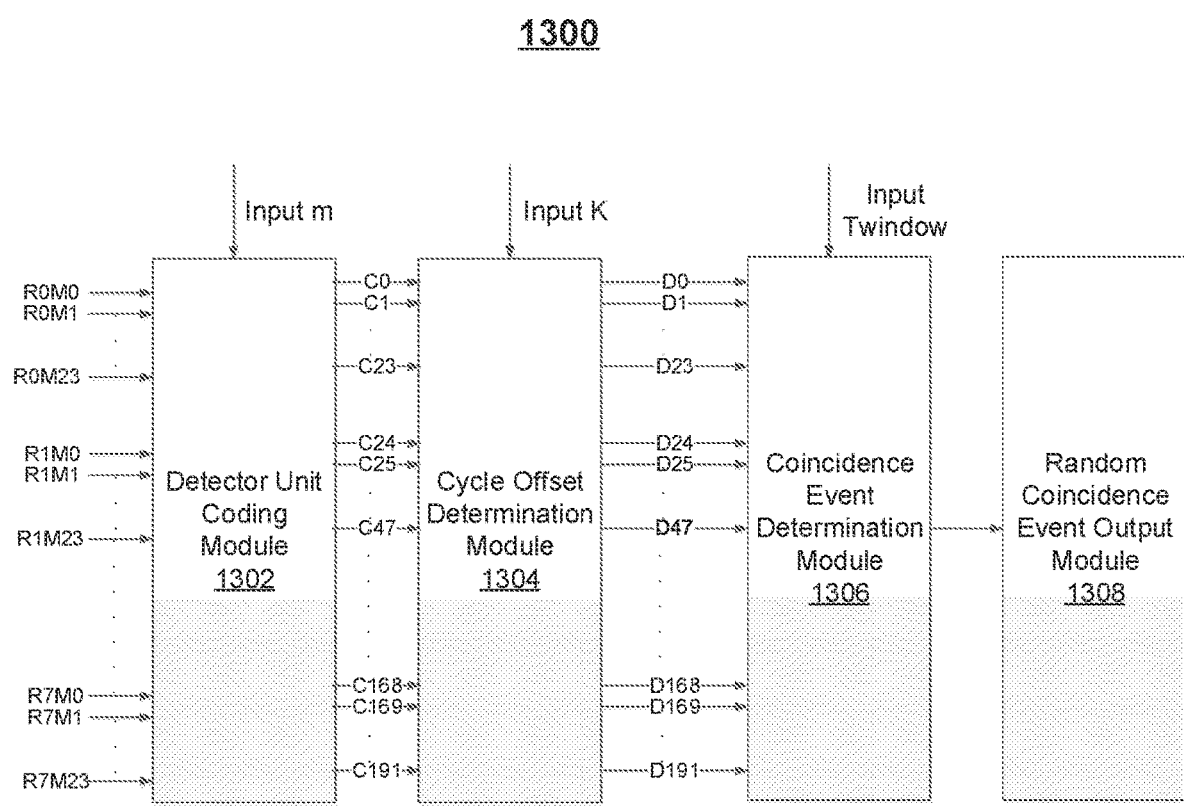
FIG. 13 is a schematic diagram illustrating an exemplary device for determining the random coincidence events according to some embodiments of the present disclosure.
Figure 14:
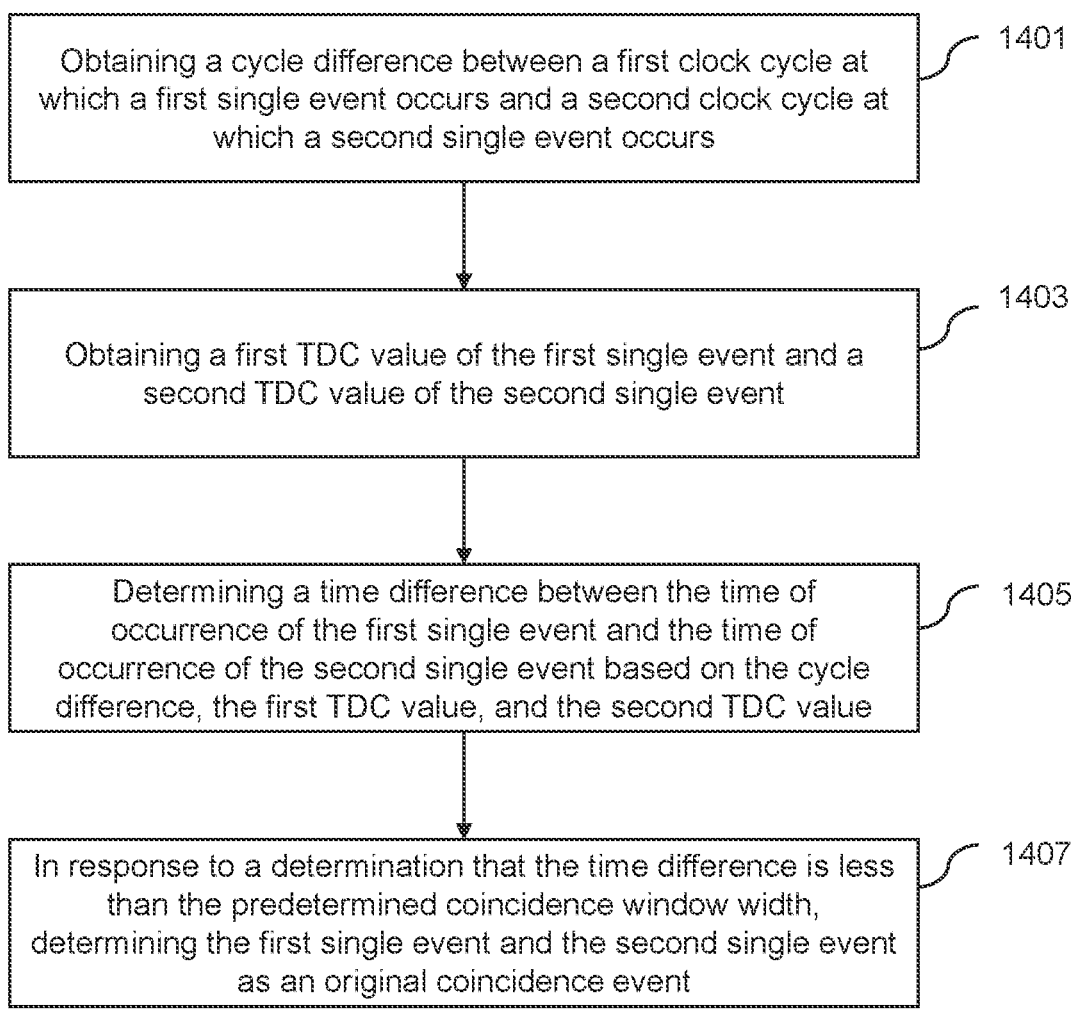
FIG. 14 is a flowchart illustrating an exemplary process for determining original coincidence events according to some embodiments of the present disclosure.

FIG. 13 is a schematic diagram illustrating an exemplary device for determining the random coincidence events according to some embodiments of the present disclosure. The detector module includes 8 detector rings. Each detector ring includes 24 detector units. The detector unit may be labelled as RxMy (x and y are integers and greater than or equal to 0). The serial number of the detector rings may be 0-7, and the serial number of the detector units may be 0-23. As shown in FIG. 14, the first detector unit on the first detector ring may be labelled as R0M0; the second detector unit on the first detector ring may be labelled as R0M1; . . . ; the 24th detector unit on the 8th detector ring may be labelled as R7M23. In order to generate the random coincidence events, different detector units may have different cycle offsets, and a difference of any two cycle offsets may be greater than the predetermined coincidence window width.

As shown in FIG. 13, the device 1300 may include a detector unit coding module 1302, a cycle offset determination module 1304, a coincidence event determination module 1306, and a random coincidence event output module 1308. In some embodiments, the number of detector units of a detector ring (labelled as m) may be inputted into the detector unit coding module 1302. The detector unit coding module 1302 may determine the coded value of each detector unit according to Equation (1). For example, for detector unit R1M1, the detector unit coding module 1302 may determine the coded value of detector unit R1M1 as 24*1+1=25. As another example, for detector unit R7M23, the detector unit coding module 1304 may determine the coded value of detector unit R7M23 as 24*7+23=191. In some embodiments, the determined coded value of each detector unit may be transmitted to the cycle offset determination module 1304. The cycle offset determination module 1304 may also obtain a coefficient K (which is an integer and greater than 0). The cycle offset determination module 1304 may determine the cycle offset of each detector unit according to Equation (3), and transmit the cycle offset of each detector unit to the coincidence event determination module 1306. The coincidence event determination module 1306 may adjust the time of occurrence of each single event according to the cycle offset of each detector unit. The coincidence event determination module 1306 may obtain a predetermined coincidence window width Twindow and determine the random coincidence events based on the adjustment of the time of occurrence of each single event and the predetermined coincidence window width Twindow. The coincidence event determination module 1306 may transmit the random coincidence events to the random coincidence event output module 1308. The random coincidence event output module 1308 may output the random coincidence events to other components of the PET system 100 (e.g., the processing device 140, the storage device 150).

In some embodiments, there may be a device for determining the original coincidence events. The device may include a coincidence event determination module and an original coincidence event output module. The coincidence event determination module may be configured to determine the original coincidence events. The original coincidence event output module may be configured to output the original coincidence events to other components of the PET system 100 (e.g., the processing device 140, the storage device 150).

FIG. 14 is a flowchart illustrating an exemplary process for determining original coincidence events according to some embodiments of the present disclosure. In some embodiments, the process 1400 can be applied for a detector module having one or more detector rings. In some embodiments, one or more operations of process 1400 may be implemented in the PET system 100 illustrated in FIG. 1. For example, the process 1400 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, the coincidence devices 500-600, one or more units of the original coincidence event determination module 1002 as illustrated in FIG. 11, or the like). As another example, a portion of the process 1400 may be implemented on the PET scanner 110. The operations of the illustrated process presented below are intended to be illustrative. In some embodiments, the process 1400 may be accomplished with one or more additional operations not described, and/or without one or more of the operations discussed. Additionally, the order in which the operations of the process 1400 as illustrated in FIG. 14 and described below is not intended to be limiting.

In 1401, the processing device 140 (e.g., the obtaining unit 1102 of the original coincidence event determination module 1002) may obtain a cycle difference between a first clock cycle at which a first single event occurs and a second clock cycle at which a second single event occurs. In some embodiments, the first single event and the second single event may be from the same detector ring, or from different detector rings. In some embodiments, the processing device 140 may determine the cycle of the clock pulse (also referred to as clock cycle) of the PET system 100 that the first single event occurs as the first clock cycle. The processing device 140 may determine the cycle of the clock pulse (also referred to as clock cycle) of the PET system 100 that the second single event occurs as the second clock cycle. The processing device 140 may then determine the cycle difference based on the first clock cycle and the second clock cycle. In some embodiments, the clock cycle of the PET system 100 may be a default value of the PET system 100. In some embodiments, the clock cycle may be 5 ns, 10 ns, 15 ns, or the like. In some embodiments, the first clock cycle and the second clock cycle may be in the same clock cycle, or in difference clock cycles.

In 1403, the processing device 140 (e.g., the obtaining unit 1102 of the original coincidence event determination module 1002) may obtain a first time-to-digital converter (TDC) value of the first single event and a second TDC value of the second single event. A TDC value of a single event may indicate the time between the occurrence time of the single event and the rising edge of the next clock cycle (e.g., the value $TDC(R_{a1}M_{b1})$ of single event $R_{a1}M_{b1}$ as shown in FIG. 18A). In some embodiments, the processing device 140 may obtain the first TDC value of the first single event and/or the second TDC value of the second single event from one or more components of the PET system 100 (e.g., the PET scanner 110, the storage device 150).

In 1405, the processing device 140 (e.g., the time difference determination unit 1104 of the original coincidence event determination module 1002) may determine a time difference between a time of occurrence of the first single event and a time of occurrence of the second single event based on the cycle difference, the first TDC value, and the second TDC value. In some embodiments, if the cycle difference is equal to 0 (i.e., the first clock cycle and the second clock cycle are in the same clock cycle), the time difference between the time occurrence of the first single event and the time of occurrence of the second single event may be an absolute value of the difference between the first TDC value and the second TDC value. Alternatively or additionally, if the cycle difference is non-zero (i.e., the first clock cycle and the second clock cycle are in different clock cycles), the processing device 140 may determine the time difference according to a time difference determination formula. The time difference determination formula may be determined according to operations 1501-1505 of process 1500.

In 1407, in response to the determination that the time difference is less than a predetermined coincidence window width, the processing device 140 (e.g., the coincidence event determination unit 1110 of the original coincidence event determination module 1002) may determine the first single event and the second single event as an original coincidence event. In some embodiments, the predetermined coincidence window width may be the maximum value of the time difference between occurrences of the coincidence events. The predetermined coincidence window width may be a default value or an empirical value related to the PET system 100. In some embodiments, the predetermined coincidence window width may be set according to a default setting of the PET system 100, or preset by a user.

In some embodiments of the present disclosure, the processing device 140 may determine the time difference between the time occurrence of the first single event and the time of occurrence of the second single event, and determine whether the first single event and the second single event are the coincidence event based on the time difference. The determination of the coincidence event can be applied for single events from the same detector ring, or single events from different detector rings. Thus, the process 1400 can be applied to determine coincidence events regardless of the number of detector rings.

In some embodiments, the process 1400 may be implemented by a hardware circuit (also called back-end processing), which is printed on a coincidence circuit board and directly connected with the detector module 116. Compared with using a sliding window at the front end, determining the coincidence events by the hardware circuit may improve the processing speed of the coincidence events.

It should be noted that the above description of the process 1400 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 140 may output the original coincidence event, which may include the time, an energy level, the location that the first single event and/or the second single event. For example, the processing device 140 may output the original coincidence event to other components of the PET system 100 (e.g., the storage device 150). In some embodiments, the processing device 140 may determine, based on a plurality of single events, a plurality of original coincidence events according to the process 1400.

In some embodiments, the present disclosure also provides a computer-readable storage medium including computer executable instructions. When the computer executable instructions are executed by a processor (e.g., the processing device 140), the computer executable instructions may direct the processor to perform acts of: determining original coincidence events based on time of occurrence of a plurality of single events; determining random coincidence events by processing the plurality of single events based on cycle offsets of detector units that detect the plurality of single events, wherein a difference of any two cycle offsets is greater than a predetermined coincidence window width; and determining the true coincidence events based on the original coincidence events and the random coincidence events.

Figure 15:
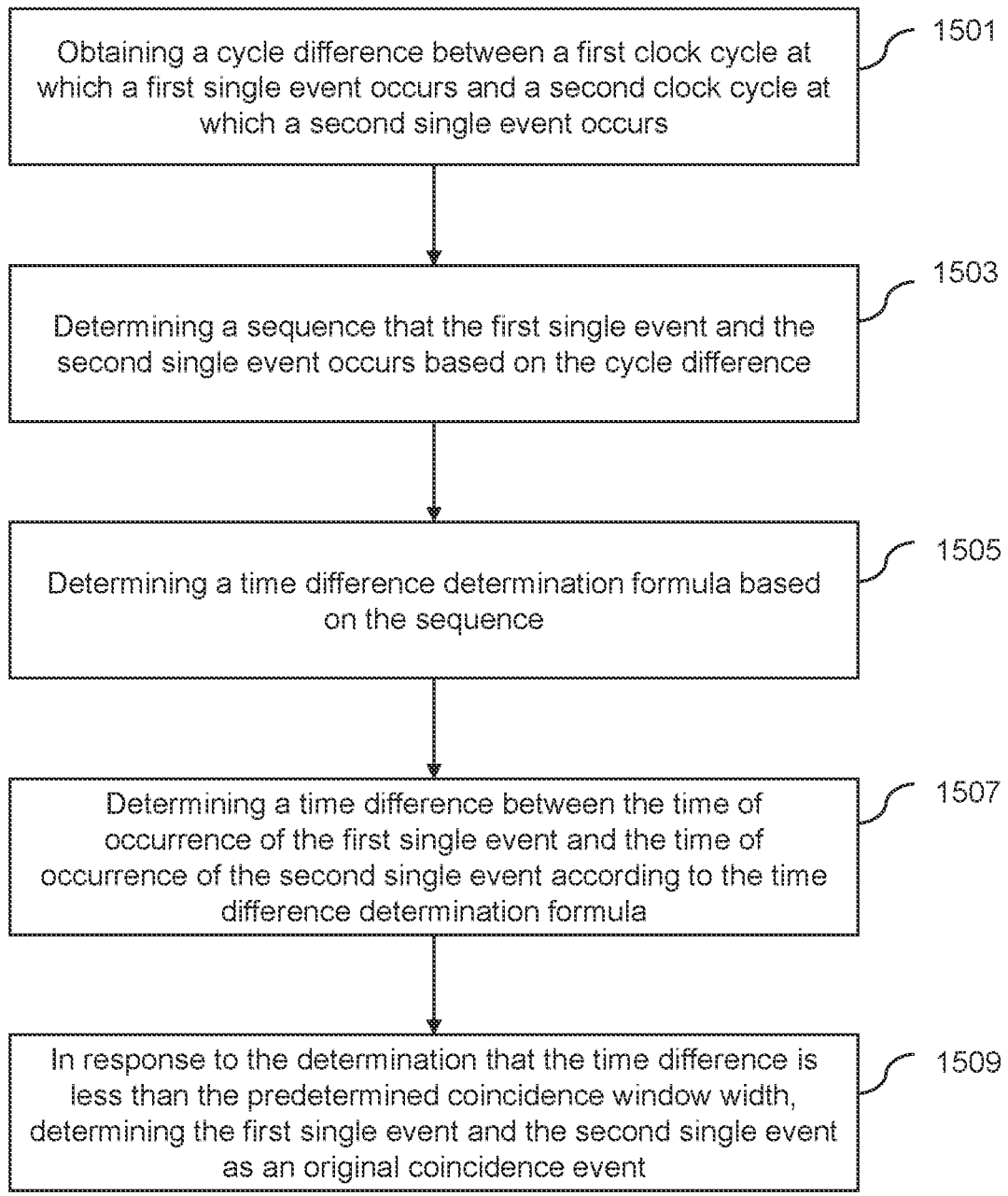
FIG. 15 is a flowchart illustrating an exemplary process for determining original coincidence events according to some embodiments of the present disclosure.

FIG. 15 is a flowchart illustrating an exemplary process for determining original coincidence events according to some embodiments of the present disclosure. In some embodiments, the process 1500 can be applied for a detector module having one or more detector rings. In some embodiments, one or more operations of process 1500 may be implemented in the PET system 100 illustrated in FIG. 1. For example, the process 1500 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, the coincidence devices 500-600, one or more units of the original coincidence event determination module 1002 as illustrated in FIG. 11, or the like). As another example, a portion of the process 1500 may be implemented on the PET scanner 110. The operations of the illustrated process presented below are intended to be illustrative. In some embodiments, the process 1500 may be accomplished with one or more additional operations not described, and/or without one or more of the operations discussed. Additionally, the order in which the operations of the process 1500 as illustrated in FIG. 15 and described below is not intended to be limiting.

In 1501, the processing device 140 (e.g., the obtaining unit 1002 of the original coincidence event determination module 1002) may obtain a cycle difference between a first clock cycle at which a first single event occurs and a second clock cycle at which a second single event occurs. In some embodiments, operation 1501 may be performed in a similar manner with operation 1401, and the descriptions are not repeated.

Figure 17A:
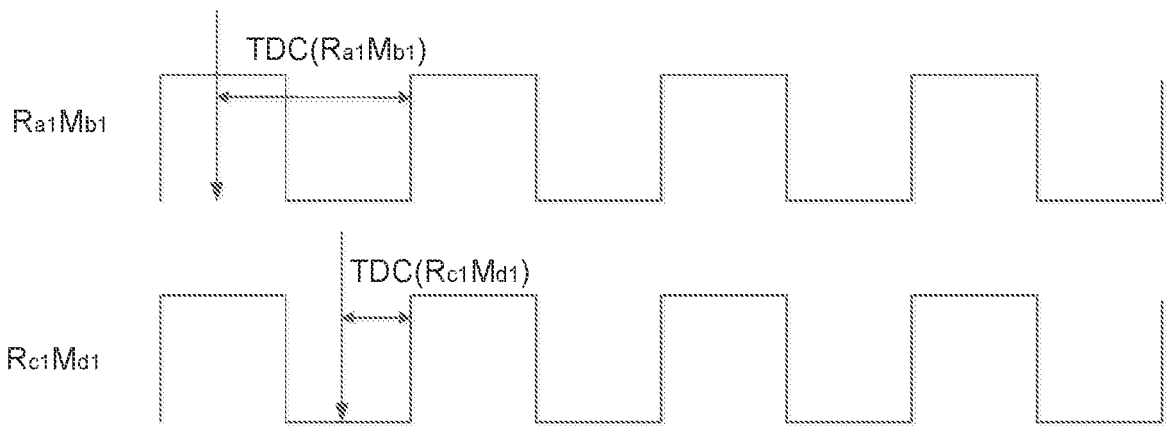
FIGS. 17A-17F are schematic diagrams illustrating exemplary coincidence events according to some embodiments of the present disclosure.
Figure 17B:
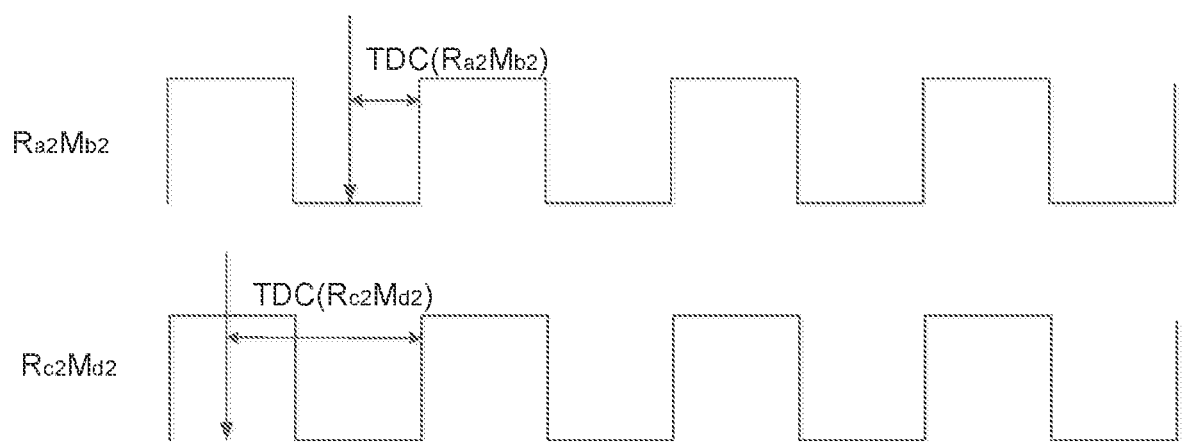

In 1503, the processing device 140 (e.g., the sequence determination unit 1106 of the original coincidence event determination module 1002) may determine a sequence that the first single event and the second single event occurs based on the cycle difference. In some embodiments, the processing device 140 may determine the sequence based on the cycle difference. If the cycle difference is greater than 0, the first single event may occur before the second single event. If the cycle difference is less than 0, the first single event may lag behind the second single event. Alternatively or additionally, if the cycle difference is equal to 0, the processing device 140 may determine the sequence based on the first TDC value and the second TDC value. For example, if the first TDC value is greater than the second TDC value, the first single event may occur before the second single event (as shown in FIG. 17A). As another example, if the first TDC value is less than the second TDC value, the first single event may lag behind the second single event (as shown in FIG. 17B).

In 1505, the processing device 140 (e.g., the formula determination unit 1108 of the original coincidence event determination module 1002) may determine a time difference determination formula based on the sequence. In some embodiments, if the first single event occurs before the second single event, the processing device 140 may determine the time difference determination formula as follows:

$$T_A = TDC_1 + T \times N - TDC_2, \quad (4)$$

wherein $T_A$ refers to the time difference; $TDC_1$ refers to the first TDC value of the first single event; $TDC_2$ refers to the second TDC value of the second single event; T refers to the clock cycle; and N refers to the absolute value of the cycle difference (N≥0).

Alternatively or additionally, if the second single event occurs before the first single event, the processing device 140 may determine the time difference determination formula as follows:

$$T_A = TDC_2 + T \times N - TDC_1. \quad (5)$$

In 1507, the processing device 140 (e.g., the time difference determination unit 1104 of the original coincidence event determination module 1002) may determine a time difference between the time of occurrence of the first single event and the time of occurrence of the second single event according to the time difference determination formula. In some embodiments, if the first single event occurs before the second single event, the processing device 140 may put the first TDC value, the second TDC value, and the cycle difference into the time difference determination formula (4). If the second single event occurs before the first single event, the processing device 140 may put the first TDC value, the second TDC value, and the cycle difference into the time difference determination formula (5).

In 1509, in response to the determination that the time difference is less than the predetermined coincidence window width, the processing device 140 (e.g., the coincidence event determination unit 1110 of the original coincidence event determination module 1002) may determine the first single event and the second single event as an original coincidence event. For example, if the first single event occurs before the second single event, and the time difference $T_A$ is less than the predetermined coincidence window width Twindow (i.e., $TDC_1 + T \times N - TDC_2 < T_{window}$), the processing device 140 may determine the first single event and the second single event as the original coincidence event. As another example, if the second single event occurs before the first single event, and the time difference $T_A$ is less than the predetermined coincidence window width Twindow (i.e., $TDC_2 + T \times N - TDC_1 < T_{window}$), the processing device 140 may determine the first single event and the second single event as the original coincidence event.

It should be noted that the above description of the process 1500 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more other optional operations (e.g., a storing operation) may be added elsewhere in the process 1500. In the storing operation, the processing device 140 may store the time difference determination formula in a storage device (e.g., the storage device 150) disclosed elsewhere in the present disclosure.

Figure 16:
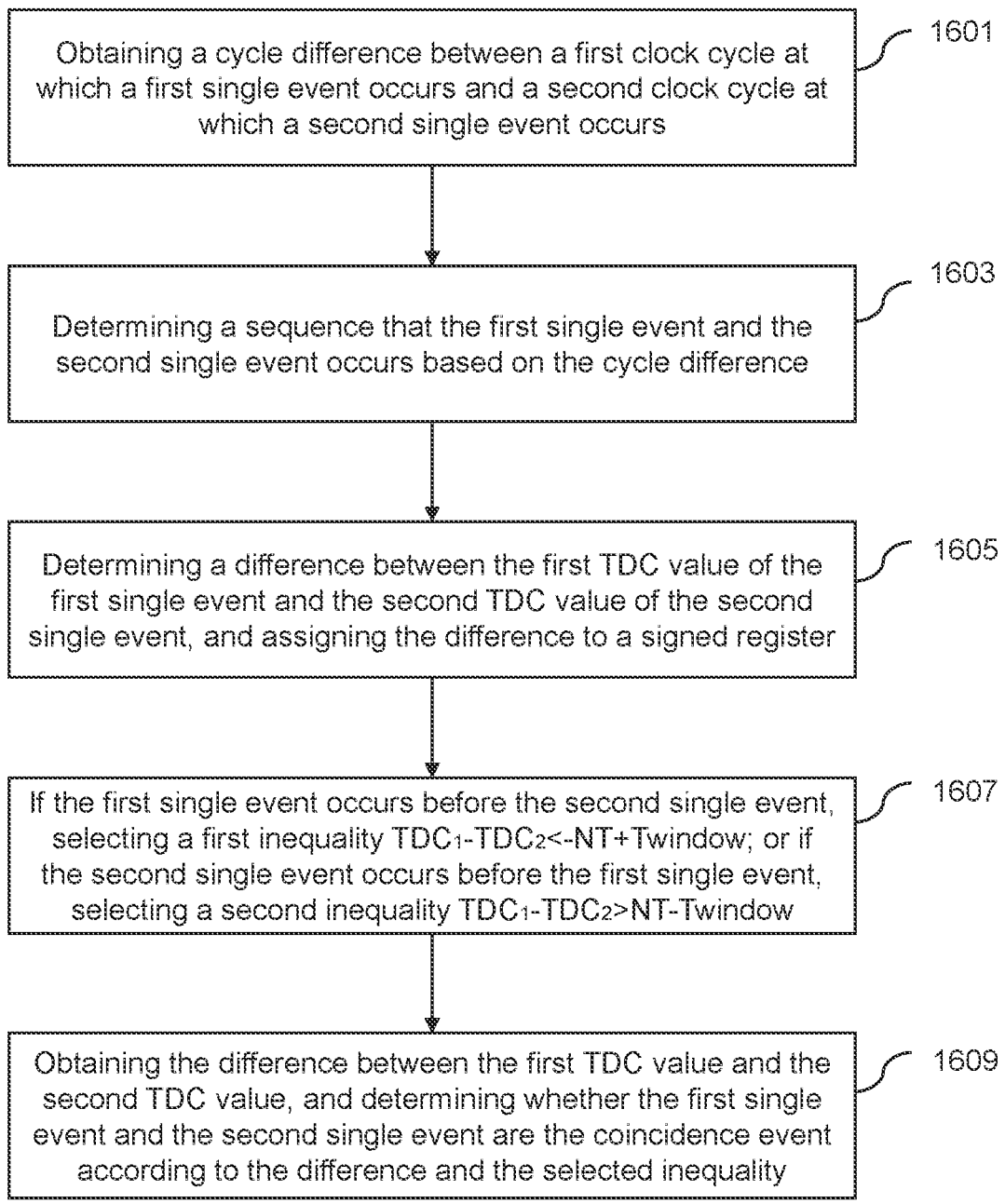
FIG. 16 is a flowchart illustrating an exemplary process for determining original coincidence events according to some embodiments of the present disclosure.

FIG. 16 is a flowchart illustrating an exemplary process for determining original coincidence events according to some embodiments of the present disclosure. In some embodiments, the process 1600 can be applied for a detector module having one or more detector rings. In some embodiments, one or more operations of process 1600 may be implemented in the PET system 100 illustrated in FIG. 1. For example, the process 1600 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, the coincidence devices 500-600, one or more units of the original coincidence event determination module 1002 as illustrated in FIG. 11, or the like). As another example, a portion of the process 1600 may be implemented on the PET scanner 110. The operations of the illustrated process presented below are intended to be illustrative. In some embodiments, the process 1600 may be accomplished with one or more additional operations not described, and/or without one or more of the operations discussed. Additionally, the order in which the operations of the process 1600 as illustrated in FIG. 16 and described below is not intended to be limiting.

In 1601, the processing device 140 (e.g., the obtaining module 1102 of the original coincidence event determination module 1002) may obtain a cycle difference between a first clock cycle at which a first single event occurs and a second clock cycle at which a second single event occurs. In some embodiments, operation 1601 may be performed in a similar manner with operation 1501 and the descriptions thereof are not repeated.

In 1603, the processing device 140 (e.g., the sequence determination module 1106) may determine a sequence that the first single event and the second single event occurs based on the cycle difference. In some embodiments, operation 1603 may be performed in a similar manner with operation 1503 and the descriptions thereof are not repeated.

In 1605, the processing device 140 (e.g., the time difference determination module 1104 of the original coincidence event determination module 1002) may determine a difference between the first TDC value of the first single event and the second TDC value of the second single event. In some embodiments, if the first TDC value is greater than the second TDC value, the difference may be a positive value. If the first TDC value is less than the second TDC value, the difference may be a negative value. The processing device 140 may assign the difference to a signed register. The signed register may be used to reflect the sign of the difference.

In 1607, if the first single event occurs before the second single event, the processing device 140 (e.g., the original coincidence event determination module 1002) may select a first inequality $TDC_1-TDC_2<-NT+Twindow$. If the second single event occurs before the first single event, the processing device 140 (e.g., the original coincidence event determination module 1002) may select a second inequality $TDC_1-TDC_2>NT-Twindow$. In some embodiments, the determination of the first inequality and the second inequality may be found elsewhere in the present disclosure (e.g., FIGS. 17A-17F and the descriptions thereof).

In 1609, the processing device 140 (e.g., the coincidence event determination unit 1110 of the original coincidence event determination module 1002) may obtain the difference between the first TDC value and the second TDC value, and determine whether the first single event and the second single event are the coincidence event according to the difference and the selected inequality (the first inequality or the second inequality). For example, for the first single event occurring before the second single event, if the difference between the first TDC value and the second TDC value satisfies the first inequality, the processing device 140 may determine the first single event and the second single event as the coincidence event. As another example, for the second single event occurring before the first single event, if the difference between the first TDC value and the second TDC value satisfies the second inequality, the processing device 140 may determine the first single event and the second single event as the coincidence event.

It should be noted that the above description of the process 1600 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, operations 1603 and 1605 may be performed simultaneously. Alternatively or additionally, operation 1605 may be performed before operation 1603.

FIGS. 17A-17F are schematic diagrams illustrating exemplary coincidence events according to some embodiments of the present disclosure. It should be noted that the descriptions below are merely for illustration purposes, and are not intended to limit the scope of the present disclosure. As used herein, $R_{a1}M_{b1}$ refers to the b1th detector unit in the a1th detector ring. $R_{a2}M_{b2}$ refers to the b2th detector unit in the a2th detector ring. $R_{a3}M_{b3}$ refers to the b3th detector unit in the a3th detector ring. $R_{a4}M_{b4}$ refers to the b4th detector unit in the a4th detector ring. $R_{a5}M_{b5}$ refers to the b5th detector unit in the a5th detector ring. $R_{a6}M_{b6}$ refers to the b6th detector unit in the a6th detector ring. $R_d M_{d1}$ refers to the d1th detector unit in the c1th detector ring. $R_{c2}M_{d2}$ refers to the d2th detector unit in the c2th detector ring. $R_{c3}M_{d3}$ refers to the d3th detector unit in the c3th detector ring. $R_{b4}M_{d4}$ refers to the d4th detector unit in the c4th detector ring. $R_{c5}M_{d5}$ refers to the d5th detector unit in the c5th detector ring. $R_{c6}M_{d6}$ refers to the d6th detector unit in the c6th detector ring.

As shown in FIG. 17A, a single event (also labelled as $R_{a1}M_{b1}$) detected by the detector unit $R_{a1}M_{b1}$ and a single event (also labelled as $R_d M_{d1}$) detected by detector unit $R_{b1}M_{d1}$ are in the same clock cycle, and the single event $R_{a1}M_{b1}$ occurs before the single event $R_{b1}M_{d1}$. If the single events $R_{a1}M_{b1}$ and $R_{b1}M_{d1}$ are the coincidence event, the time difference between the time of occurrence of the single event $R_{a1}M_{b1}$ and the time of occurrence of the single event $R_{c1}M_{d1}$ should be less than the predetermined coincidence window width. That is, $T_{\Delta\_1}=TDC(R_{a1}M_{b1})-TDC(R_{c1}M_{d1})<T_{window}$.

As shown in FIG. 17B, a single event (also labelled as $R_{a2}M_{b2}$) detected by the detector unit $R_{a2}M_{b2}$ and a single event (also labelled as $R_{c2}M_{d2}$) detected by the detector unit $R_{c2}M_{d2}$ are in the same clock cycle, and the single event $R_{c2}M_{d2}$ occurs before the single event $R_{a2}M_{b2}$. If the single events $R_{a2}M_{b2}$ and $R_{c2}M_{d2}$ are the coincidence event, the time difference between the time of occurrence of the single event $R_{a2}M_{b2}$ and the time of occurrence of the single event $R_{c2}M_{d2}$ should be less than the predetermined coincidence window width. That is, $T_{\Delta\_2}=TDC(R_a M_{d2})-TDC(R_{a2}M_{b2})<T_{window}$.

Thus, if two single events (a first single event and a second single event) are in the same clock cycle and the two single events are the coincidence event, the time difference between the time of occurrence of the two single events should be less than the predetermined coincidence window width. That is, $|TDC_1-TDC_2|<Twindow$, wherein $TDC_1$ is the TDC value of the first single event; $TDC_2$ is the TDC value of the second single event. The inequality can be transformed into $-Twindow<TDC_1-TDC_2<Twindow$.

Figure 17C:
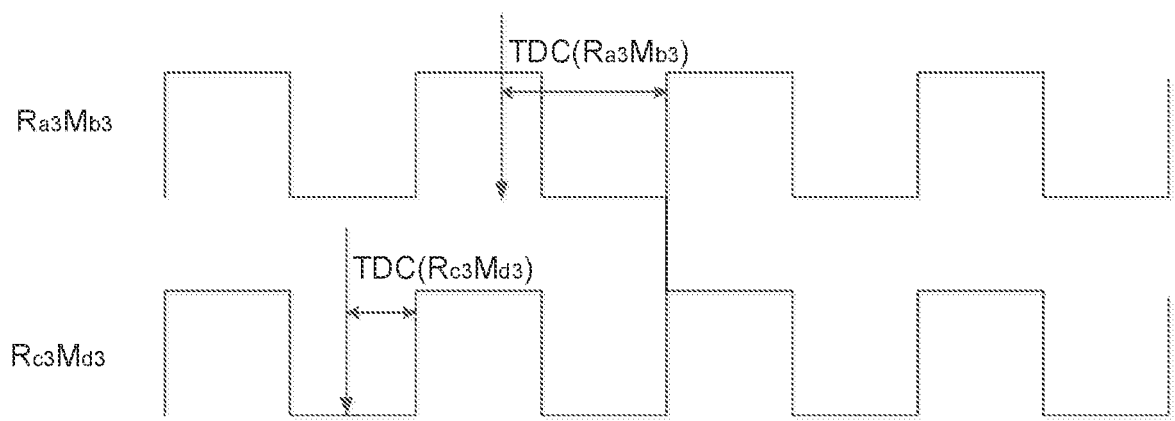

As shown in FIG. 17C, a single event (also labelled as $R_{a3}M_{b3}$) detected by the detector unit $R_{a3}M_{b3}$ and a single event (also labelled as $R_{c3}M_{d3}$) detected by the detector unit $R_{c3}M_{d3}$ are in different clock cycles, and the cycle difference is one clock cycle T. The single event $R_{c3}M_{d3}$ occurs before the single event $R_{a3}M_{b3}$. If the single events $R_{a3}M_{b3}$ and $R_{c3}M_{d3}$ are the coincidence event, the time difference between the time of occurrence of the single event $R_{a3}M_{b3}$ and the time of occurrence of the single event $R_{c3}M_{d3}$ should be less than the predetermined coincidence window width. That is, $T_{\Delta\_a}=TDC(R_{c3}M_{d3})+T-TDC(R_{a3}M_{b3})<T_{window}$. The inequality can be transformed into $TDC(R_{a3}M_{b3})-TDC(R_{c3}M_{d3})>-T_{window}+T$.

Figure 17D:
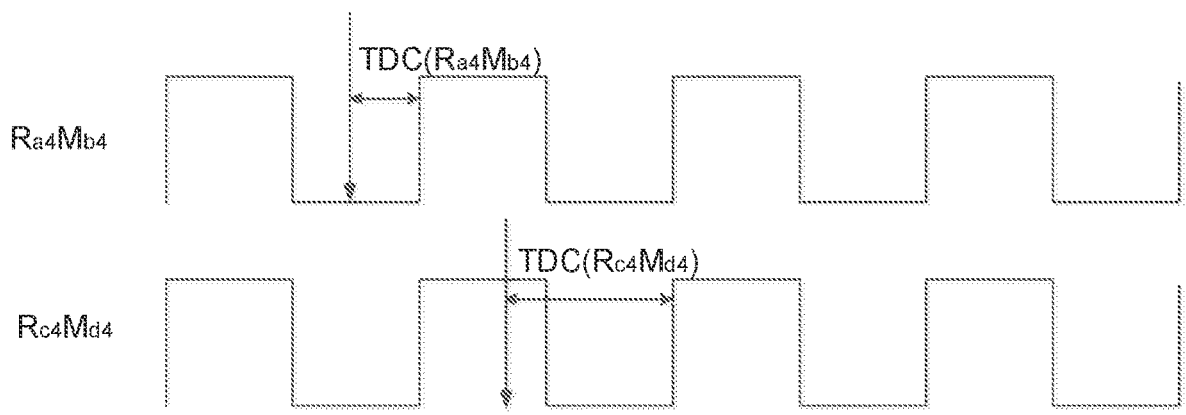

As shown FIG. 17D, a single event (also labelled as $R_{a4}M_{b4}$) detected by the detector unit $R_{a4}M_{b4}$ and a single event (also labelled as $R_{c4}M_{d4}$) detected by the detector unit $R_{c4}M_{d4}$ are in different clock cycles, and the cycle difference is one clock cycle T. The single event $R_{a4}M_{b4}$ occurs before the single event $R_{c4}M_{d4}$. If the single events $R_{a4}M_{b4}$ and $R_{c4}M_{d4}$ are the coincidence event, the time difference between the time of occurrence of the single event $R_{a4}M_{b4}$ and the time of occurrence of the single event $R_{c4}M_{d4}$ should be less than the predetermined coincidence window width. That is, $T_{\Delta 4}=TDC(R_{a4}M_{b4})+T-TDC(R_{c4}M_{d4})<T_{window}$. The inequality can be transformed into $TDC(R_{a4}M_{b4})-TDC(R_{c4}M_{d4})<T_{window}-T$.

Figure 17E:
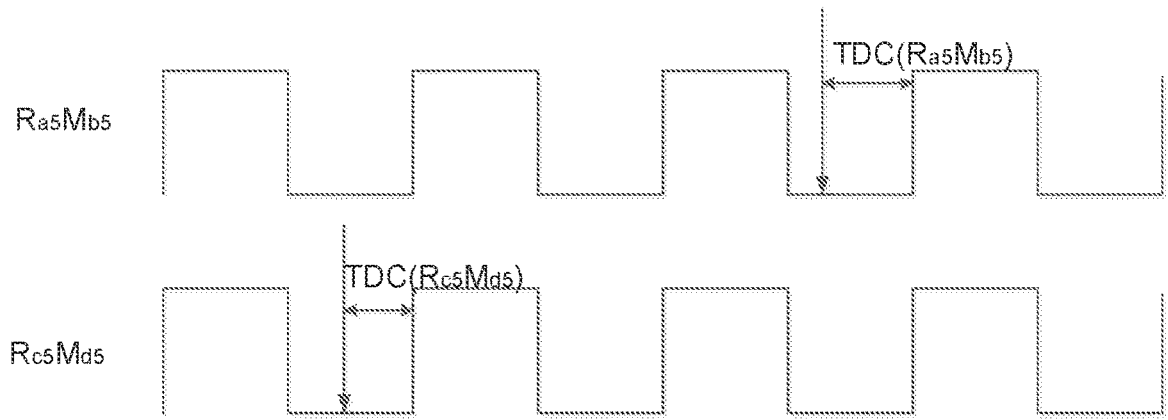

As shown in FIG. 17E, a single event (also labelled as $R_{a5}M_{b5}$) detected by the detector unit $R_{a5}M_{b5}$ and a single event (also labelled as $R_{c5}M_{d5}$) detected by the detector unit $R_{c5}M_{d5}$ are in different clock cycles, and the cycle difference is two clock cycle 2T. The single event $R_{c5}M_{d5}$ occurs before the single event $R_{a5}M_{b5}$. If the single events $R_{a5}M_{b5}$ and $R_{c5}M_{d5}$ are the coincidence event, the time difference between the time of occurrence of the single event $R_{a5}M_{b5}$ and the time of occurrence of the single event $R_{c5}M_{d5}$ should be less than the predetermined coincidence window width.

That is, $T_{\Delta5}=TDC(R_{c5}M_{d5})+2T-TDC(R_{a5}M_{b5})<T_{window}$. The inequality can be transformed into $TDC(R_{a5}M_{b5})-TDC(R_{c5}M_{d5})>-T_{window}+2T$.

Figure 17F:
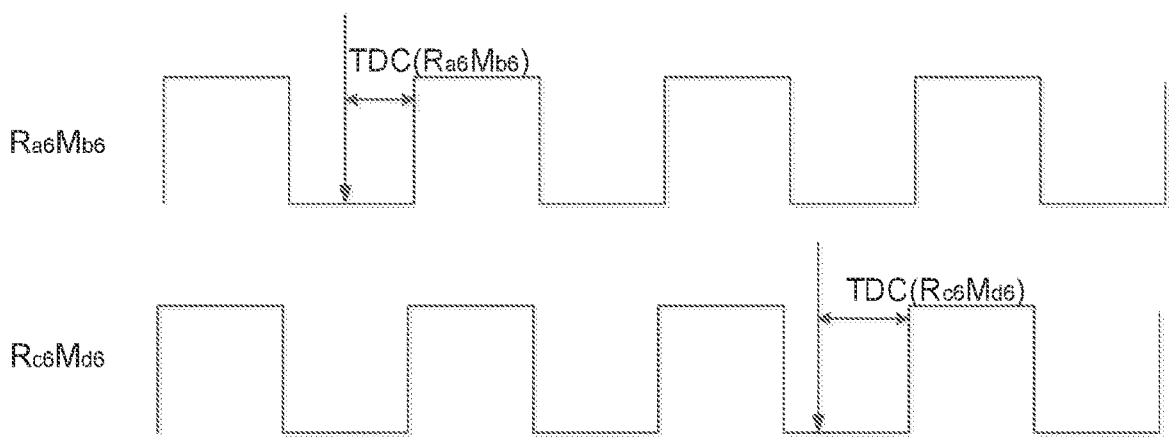

As shown in FIG. 17F, a single event (also labelled as $R_{a6}M_{b6}$) detected by the detector unit $R_{a6}M_{b6}$ and a single event (also labelled as $R_{c6}M_{d6}$) detected by the detector unit $R_{c6}M_{d6}$ are in different clock cycles, and the cycle difference is two clock cycle 2T. The single event $R_{a6}M_{b6}$ occurs before the single event $R_{c6}M_{d6}$. If the single events $R_{a6}M_{b6}$ and $R_{c6}M_{d6}$ are the coincidence event, the time difference between the time of occurrence of the single event $R_{a6}M_{b6}$ and the time of occurrence of the single event $R_{c6}M_{d6}$ should be less than the predetermined coincidence window width. That is, $T_{\Delta6}=TDC(R_{a6}M_{b6})+2T-TDC(R_{c6}M_{d6})<T_{window}$. The inequality can be transformed into $TDC(R_{a6}M_{b6})-TDC(R_{c6}M_{d6})<T_{window}-2T$.

Thus, in some embodiments, two single events (e.g., a first single event and a second single event) may be in different clock cycles, and the cycle difference may be N (N>0). If the second single event occurs before the first single event and the two single events are the coincidence event, the time difference between the time of occurrence of the two single events should be less than the predetermined coincidence window width. That is, $TDC_2+N*T-TDC_1<Twindow$, wherein $TDC_1$ is the TDC value of the first single event; $TDC_2$ is the TDC value of the second single event. The inequality can be transformed into $TDC_1-TDC_2>N*T-Twindow$.

Alternatively or additionally, two single events (e.g., a first single event and a second single event) may be in different clock cycles, and the cycle difference may be N (N>0). If the first single event occurs before the second single event and the two single events are the coincidence event, the time difference between the time of occurrence of the two single events should be less than the predetermined coincidence window width. That is, $TDC_1+N*T-TDC_2<Twindow$, wherein $TDC_1$ is the TDC value of the first single event; $TDC_2$ is the TDC value of the second single event. The inequality can be transformed into $TDC_1-TDC_2<-N*T+Twindow$.

In some embodiments, each detector unit may correspond to a cycle offset. The cycle offsets of different detector units may be different. A difference of any two cycle offsets may be greater than the predetermined coincidence window width. Thus, after the time of occurrence of single event(s) is adjusted by its corresponding cycle offsets, the original coincidence events must be converted into non-coincidence events. A portion of original non-coincidence events may be converted into coincidence events. FIGS. 18A-18D are schematic diagrams illustrating the adjustment of single events according to some embodiments of the present disclosure. It should be noted that the descriptions below are merely for illustration purposes, and are not intended to limit the scope of the present disclosure. As used herein, $R_{s1}M_{t1}$ refers to the t1th detector unit in the s1th detector ring. $R_{s2}M_{t2}$ refers to the t2th detector unit in the s2th detector ring. $R_{u1}M_{v1}$ refers to the v1th detector unit in the u1th detector ring. $R_{u2}M_{v2}$ refers to the v2th detector unit in the u2th detector ring. Merely by way of example, the predetermined coincidence window width Twindow may be 2T. T refers to the clock cycle.

As shown in FIG. 18A, a single event (also labelled as $R_{s1}M_{t1}$) detected by the detector unit $R_{s1}M_{t1}$ and the single event (also labelled as $R_{u1}M_{v1}$) detected by the detector unit $R_{u1}M_{v1}$ are in the same clock cycle. The time difference between the time of occurrence of the single event $R_{s1}M_{t1}$ and the time of occurrence of the single event $R_{u1}M_{v1}$ is less than the predetermined coincidence window width Twindow (2T). That is, the single event $R_{s1}M_{t1}$ and the single event $R_{u1}M_{v1}$ are the coincidence event. As shown in FIG. 18B, the time of occurrence of the single event $R_{u1}M_{v1}$ are adjusted by increasing an cycle offset (e.g., 3T). After the adjustment, the single event $R_{s1}M_{t1}$ and the single event $R_{u1}M_{v1}$ are in different clock cycles, and the cycle difference is 3 clock cycles. The time difference between the time of occurrence of the single event $R_{s1}M_{t1}$ and the adjusted time of occurrence of the single event $R_{u1}M_{v1}$ is greater than the predetermined coincidence window width Twindow (2T). Thus, the single event $R_{s1}M_{t1}$ and the single event $R_{u1}M_{v1}$ becomes the non-coincidence event.

As shown in FIG. 18C, a single event (also labelled as $R_{s2}M_{t2}$) detected by the detector unit $R_{s2}M_{t2}$ and the single event (also labelled as $R_{u2}M_{v2}$) detected by the detector unit $R_{u2}M_{v2}$ are in different clock cycles, and the cycle difference is 3 clock cycles. The time difference between the time of occurrence of the single event $R_{s2}M_{t2}$ and the time of occurrence of the single event $R_{u2}M_{v2}$ is greater than the predetermined coincidence window width Twindow (2T). That is, the single event $R_{s2}M_{t2}$ and the single event $R_{u2}M_{v2}$ are the non-coincidence event. As shown in FIG. 18D, the time of occurrence of the single event $R_{u2}M_{v2}$ are adjusted by increasing an cycle offset (e.g., 3T). After the adjustment, the single event $R_{s2}M_{t2}$ and the single event $R_{u2}M_{v2}$ are in the same clock cycle. The time difference between the time of occurrence of the single event $R_{s2}M_{t2}$ and the adjusted time of occurrence of the single event $R_{u2}M_{v2}$ is less than the predetermined coincidence window width Twindow (2T). Thus, the single event $R_{s2}M_{t2}$ and the single event $R_{u2}M_{v2}$ becomes the coincidence event.

Figure 19:
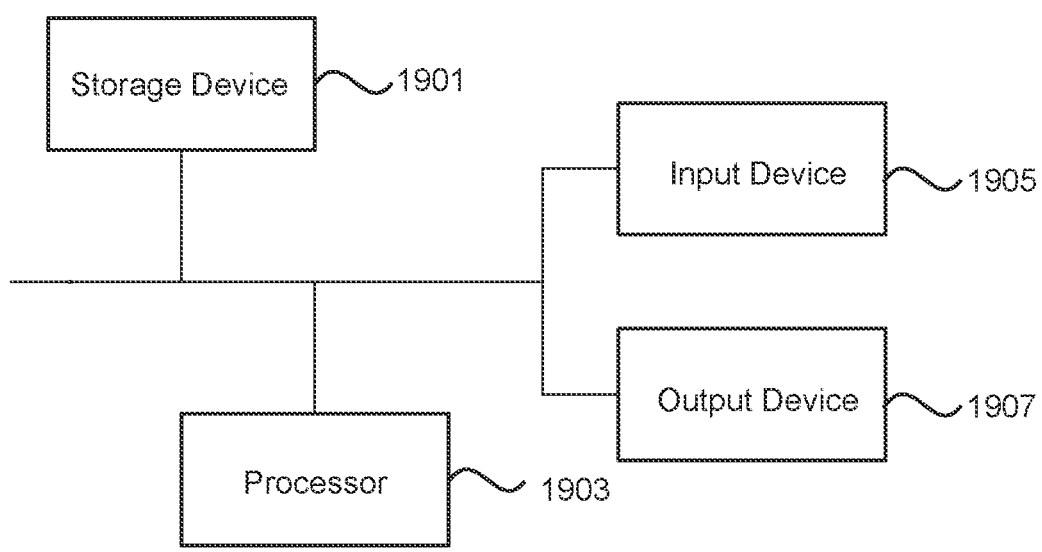
FIG. 19 is a structural diagram of a device according to some embodiments of the present disclosure.

FIG. 19 is a structural diagram of a device according to some embodiments of the present disclosure. As shown in FIG. 19, the device 1900 may include a storage device 1901, a processor 1903, an input device 1905, and an output device 1907. In some embodiments, the device 1900 may include multiple processors 1903. For briefly, only one processor 1903 is shown in FIG. 19. In some embodiments, the storage device 1901, the processor 1903, the input device 1905, and the output device 1907 may be connected via a bus. It should be noted that the storage device 1901, the processor 1903, the input device 1905, and the output device 1907 may be connected via other ways (e.g., a network). The network may include the Internet, an intranet, a local area network (LAN), a mobile communication network (e.g., 3G, 4G, 5G), or the like, or any combination thereof.

In some embodiments, the storage device 1901 may include a computer-readable storage medium, which is configured to store software programs, executable programs and modules. For example, the storage device 1901 may store the program instructions, modules (e.g., the original coincidence event determination module 1002, the random coincidence event determination module 1004, the true coincidence event determination module 1006), and/or units (e.g., the obtaining unit 1102, the time difference determination unit 1104, the sequence determination unit 1106, the formula determination unit 1108, and the coincidence event determination unit 1110) described in the present disclosure. The processor 1903 may run the program instructions, modules and/or units stored in the storage device 1901 to perform the processes 1200, 1400-1600.

The storage device 1901 may include a program area and a data area. The program area may store operation systems, application programs, etc. The data area may store data generated during the processing process. In some embodiments, the storage device 1901 may also include a high-speed random access memory (RAM), a non-volatile memory (e.g., magnetic disk, a flash, or other non-volatile solid-state storage device).

In some embodiments, the input device 1905 may be configured to receive numeric or character information, and generate key signal inputs related to user settings and function control of the device. The output device 1907 may include a display device, such as a display screen.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A device for determining coincidence events in a PET system, comprising:
   one or more detector rings; and
   one or more coincidence modules, each coincidence module corresponding to one of the one or more detector rings, and the one or more coincidence modules are connected in one-to-one correspondence with the one or more detector rings, respectively, the one or more coincidence modules being configured to determine coincidence events based on single events detected by the one or more detector rings, wherein:
   the coincidence events determined by a coincidence module include first coincidence events and second coincidence events, wherein:
     a first coincidence event includes two first single events that are corresponding to each other, and
     a second coincidence event includes a first single event and a second single event, the first single event being a single event from a detector ring corresponding to the coincidence module and the second single event being a single event from a detector ring not corresponding to the coincidence module.

2. The device of claim 1, wherein the coincidence module includes a first coincidence unit and a second coincidence unit, wherein:
   the first coincidence unit is configured to obtain multiple first single events and determine multiple first coincidence events based on the multiple first single events; and
   the second coincidence unit is configured to obtain multiple first single events and multiple second single events and determine multiple second coincidence events based on the multiple first single events and the multiple second signal events.

3. The device of claim 2, wherein the second coincidence events are true coincidence events, wherein to determine multiple second coincidence events, the second coincidence unit is further configured to:
   determine original coincidence events based on the occurrence time of the first single events and the second single events;
   determine random coincidence events by processing the first single events and the second single events based on cycle offsets of detector units that detect the first single events and the second single events, wherein the difference between any two cycle offsets is greater than a predetermined coincidence window width; and
   determine the true coincidence events based on the original coincidence events and the random coincidence events.

4. The device of claim 3, wherein each cycle offset is an integer multiple of a clock cycle, and the cycle offsets are different from each other.

5. The device of claim 3, wherein the cycle offset of each detector unit includes a coded value of the detector unit and a parameter value of the detector unit, the coded values of different detector units are different.

6. The device of claim 1, further comprising at least one reconstruction module, wherein the at least one reconstruction module is connected to the one or more coincidence modules and is configured to receive the coincidence events and reconstruct an image based on the coincidence events.

7. The device of claim 6, further comprising a control and transmission module, wherein the control and transmission module is disposed between the one or more coincidence modules and the at least one reconstruction module and is configured to receive the coincidence events and transmit the coincidence events to the at least one reconstruction module.

8. The device of claim 7, further comprising a control module, wherein the control module is connected to the control and transmission module and is configured to transmit an instruction to the control and transmission module.

9. The device of claim 1, further comprising an interconnection module connected to the one or more coincidence modules, wherein the interconnection module is configured to store the single events detected by the one or more detector rings, and a coincidence module is configured to obtain second single events from the interconnection module.

10. The device of claim 1, wherein the one or more coincidence modules are further configured to determine a second coincident event by:
    obtaining a cycle difference between a first clock cycle at which the first single event of the second coincidence event occurs and a second clock cycle at which the second single event of the second coincidence event occurs;
    obtaining a first time-to-digital converter (TDC) value of the first single event and a second TDC value of the second single event;
    determining a time difference between a time of occurrence of the first single event and a time of occurrence of the second single event based on the cycle difference, the first TDC value, and the second TDC value; and
    in response to a determination that the time difference is less than the predetermined coincidence window width, determine the first single event and the second single event as the second coincident event.

11. The device of claim 10, wherein the first clock cycle and the second clock cycle are in difference clock cycles.

12. A method for determining true coincidence events, implemented on a computing device including at least one processor, at least one storage device, and a communication platform connected to a network, comprising:
    determining original coincidence events based on time of occurrence of a plurality of single events;
    determining random coincidence events by processing the plurality of single events based on cycle offsets of detector units that detect the plurality of single events, wherein a difference of any two cycle offsets is greater than a predetermined coincidence window width; and determining the true coincidence events based on the original coincidence events and the random coincidence events, wherein the determining original coincidence events comprises:

obtaining a cycle difference between a first clock cycle at which a first single event occurs and a second clock cycle at which a second single event occurs;

obtaining a first time-to-digital converter (TDC) value of the first single event and a second TDC value of the second single event;

determining a time difference between a time of occurrence of the first single event and a time of occurrence of the second single event based on the cycle difference, the first TDC value, and the second TDC value; and in response to a determination that the time difference is less than the predetermined coincidence window width, determining the first single event and the second single event as an original coincidence event.

13. The method of claim 12, wherein the determining random coincidence events by processing the plurality of single events based on cycle offsets of detector units that detect the plurality of single events comprises:

for each single event of the plurality of single events,
obtaining a cycle offset of a detector unit that detect the single event;
adjusting the time of occurrence of the single event by increasing the cycle offset to the time of occurrence of the single event; and determining the random coincidence events based on the adjustment of the time of occurrence of each single event.

14. The method of claim 12, wherein the cycle offset of the detector unit includes a coded value of the detector unit and a parameter value of the detector unit, wherein the coded values of different detector units are different.

15. The method of claim 14, wherein the parameter value of the detector unit is an integer multiple of a clock cycle and is greater than the predetermined coincidence window width.

16. The method of claim 14, wherein the plurality of single events are detected by one or more detector rings, and each of the one or more detector rings includes a plurality of detector units, wherein the coded value of a detector unit is expressed as m*X+Y, wherein m refers to the number of detector units of a detector ring, X refers to the serial number of detector ring, Y refers to the serial number of detector unit.

17. The method of claim 12, wherein the determining a time difference between the time of occurrence of the first single event and the time of occurrence of the second single event comprises:

determining a sequence that the first single event and the second single event occurs based on the cycle difference;

determining a time difference determination formula based on the sequence; and determining the time difference between the time of occurrence of the first single event and the time of occurrence of the second single event according to the time difference determination formula.

18. The method of claim 12, further comprising:
outputting the original coincidence event, which includes a time, an energy level, a location of the first single event and/or the second single event.

19. A system for determining true coincidence events, comprising:

at least one storage device including a set of instructions;

at least one processor in communication with the at least one storage device, wherein when executing the set of instructions, the at least one processor is configured to cause the system to:

determine original coincidence events based on time of occurrence of a plurality of single events;

determine random coincidence events by processing the plurality of single events based on cycle offsets of detector units that detect the plurality of single events, wherein a difference of any two cycle offsets is greater than a predetermined coincidence window width; and determine the true coincidence events based on the original coincidence events and the random coincidence events, wherein to determine original coincidence events, the at least one processor is further configured to cause the system to:

obtain a cycle difference between a first clock cycle at which a first single event occurs and a second clock cycle at which a second single event occurs;

obtain a first time-to-digital converter (TDC) value of the first single event and a second TDC value of the second single event;

determine a time difference between a time of occurrence of the first single event and a time of occurrence of the second single event based on the cycle difference, the first TDC value, and the second TDC value; and in response to a determination that the time difference is less than the predetermined coincidence window width, determine the first single event and the second single event as an original coincidence event.

* * * * *